United States Patent [19]

Takahashi et al.

[11] Patent Number: 6,156,177
[45] Date of Patent: *Dec. 5, 2000

[54] DNA DETECTOR AND DNA DETECTION METHOD

[75] Inventors: Satoshi Takahashi, Kokubunji; Hideki Kambara, Hachiouji, both of Japan

[73] Assignee: Hitachi, Ltd., Tokyo, Japan

[ * ] Notice: This patent is subject to a terminal disclaimer.

[21] Appl. No.: 09/525,024

[22] Filed: Mar. 14, 2000

Related U.S. Application Data

[63] Continuation of application No. 09/400,438, Sep. 21, 1999, which is a continuation of application No. 09/088,849, Jun. 2, 1998, Pat. No. 5,954,932, which is a continuation of application No. 08/669,915, Jun. 25, 1996, Pat. No. 5,759,374, which is a continuation of application No. 08/337,412, Nov. 7, 1994, Pat. No. 5,529,679, which is a continuation of application No. 08/051,324, Apr. 23, 1993, abandoned, which is a continuation-in-part of application No. 08/026,592, Mar. 5, 1993, Pat. No. 5,314,602, which is a continuation of application No. 07/843,232, Feb. 28, 1992, Pat. No. 5,268,080.

[30] Foreign Application Priority Data

Feb. 28, 1991 [JP] Japan ......... 3-34006
Apr. 24, 1992 [JP] Japan ......... 4-106966
Sep. 10, 1992 [JP] Japan ......... 4-241727

[51] Int. Cl.$^7$ ......... G01N 27/26; G01N 27/447
[52] U.S. Cl. ......... 204/452; 204/603
[58] Field of Search ......... 204/451, 452, 204/453, 454, 455, 601, 602, 603, 604, 605

[56] References Cited

U.S. PATENT DOCUMENTS

| | | | |
|---|---|---|---|
| 3,764,512 | 10/1973 | Greenword et al. ......... | 204/645 |
| 4,675,095 | 6/1987 | Kambara et al. ......... | 204/612 |
| 4,929,329 | 5/1990 | Danby et al. ......... | 204/608 |
| 4,938,593 | 7/1990 | Morris et al. ......... | 356/344 |

(List continued on next page.)

FOREIGN PATENT DOCUMENTS

| | | |
|---|---|---|
| 3-264859 | 11/1991 | Japan . |
| 88/07888 | 11/1991 | WIPO . |
| 94/29712 | 12/1994 | WIPO . |

OTHER PUBLICATIONS

Harold Swerdlow et al, "Three DNA Sequencing Methods Using Capillary Gel Electrophoresis and Laser–Induced Fluorescence" Analytical Chemistry, vol. 63, No. 24, pp. 2835–2841, Dec. 15, 1991.

Harold Swerdlow et al, "Capillary gel electrophoresis for rapid high resolution DNA sequencing" Nucleic Acids Research, vol. 18, No. 6, pp. 1415–1419, 1990, No month available.

(List continued on next page.)

*Primary Examiner*—Maureen M. Wallenhorst
*Assistant Examiner*—John S Starsiak
*Attorney, Agent, or Firm*—Antonelli, Terry, Stout & Kraus, LLP

[57] ABSTRACT

A method for analyzing samples includes the steps of introducing samples labeled with fluorophores into a first end of each of a plurality of electrophoresis lanes including a separation medium, a second end of each of the electrophoresis lanes being disposed in an optical cell filled with a buffer solution, applying an electric field to the electrophoresis lanes to separate the samples labeled with the fluorophores and cause the separated samples labeled with the fluorophores to migrate through the electrophoresis lanes into the buffer solution in the optical cell, exciting, with light from a light source, the fluorophores labeling the separated samples in the buffer solution in the optical cell to emit fluorescence in the buffer solution in the optical cell, and detecting, with a photodetector, the fluorescence emitted by the fluorophores labeling the separated samples in the buffer solution in the optical cell. The light source is selected from the group consisting of a He—Ne laser which emits light having a wavelength of 594 nm, a He—Ne laser which emits light having a wavelength of 632.8 nm, a YAG laser which emits light having a wavelength of 532 nm, and a semiconductor laser which emits light having a wavelength of 670 nm.

4 Claims, 8 Drawing Sheets

U.S. PATENT DOCUMENTS

| | | | |
|---|---|---|---|
| 5,062,942 | 11/1991 | Kambara et al. | 204/612 |
| 5,108,170 | 4/1992 | Myers | 356/344 |
| 5,108,179 | 4/1992 | Myers | 356/344 |
| 5,192,412 | 3/1993 | Kambara et al. | 204/612 |
| 5,274,240 | 12/1993 | Mathies et al. | 250/458.1 |
| 5,439,578 | 8/1995 | Dovichi et al. | 204/603 |
| 5,582,705 | 12/1996 | Yeung et al. | 204/603 |
| 5,759,374 | 6/1998 | Takahashi et al. | 204/603 |
| 5,954,932 | 9/1999 | Takahashi et al. | 204/452 |

OTHER PUBLICATIONS

L. Smith et al, "Fluorescence detection in automated DNA sequence analysis", Nature, pp. 674–679, Jun. 12, 1986.

H. Kambara et al, "Optimization of Parameters in a DNA Sequertor Using Fluorescence Detection" Bio/Technology, vol. 6, pp. 816–821, Jul. 1988.

Y. Cheng et al, "Subattomole Amino Acid Analysis by Capillary Zone Electrophoresis and Laser–Induced Fluorescence," Science, vol. 242, pp. 562–564, Oct. 28, 1988.

L. Morrison et al, "Solution–Phase Detection of Polynucleotides Using Interacting Fluorescent Labels and Competative Hybridization" Analytical Biochemistry, vol. 183, pp. 231–232, 1988, No month available.

H. Swerdlow et al, "Capillary gel electrophoresis for DNA sequencing–Laser–induced fluorescence detection with the sheath flow cuvette" Journal of Chromatography, vol. 516, pp. 61–67, 1990, No month available.

Norman J. Dovichi et al, "Three DNA Sequencing Methods Using Capillary Gel Electrophoresis and Laser–Induced Fluorescence" Analytical Chemistry, vol. 63, No. 24, pp. 2835–2841, 1991, No month available.

L. Smith et al., "Fluorescence detection in automated DNA sequence analysis", *Nature*, vol. 321, Jun. 12, 1986, pp. 674–679.

H. Kambara et al., "Optimization of Parameters in a DNA Sequenator Using Fluorescence Detection", *Bio/Technology*, vol. 6, Jul. 1988, pp. 816–821.

Y. Cheng et al., "Subattomole Amino Acid Analysis by Capillary Zone Electrophoresis and Laser–Induced Fluorescence", *Science*, vol. 242, Oct. 28, 1988, pp. 562–564.

L. Morrison et al., "Solution–Phase Detection of Polynucleotides Using Interacting Fluorescent Labels and Competitive Hybridization", *Analytical Biochemistry*, vol. 183, 1989, pp. 231–232.

H. Swerdlow et al., "Capillary gel electrophoresis for rapid, high resolution DNA sequencing", *Nucleic Acids Research*, vol. 18, No. 6, 1990, pp. 1415–1419.

H. Swerdlow et al., "Capillary gel electrophoresis for DNA sequencing—Laser–induced fluorescence detection with the sheath flow cuvette", *Journal of Chromatography*, vol. 516, 1990, pp. 61–67.

H. Swerdlow et al., "Three DNA Sequencing Methods Using Capillary Gel Electrophoresis and Laser–Induced Fluorescence", *Analytical Chemistry*, vol. 63, No. 24, Dec. 15, 1991, pp. 2835–2841.

DNA DETECTOR AND DNA DETECTION METHOD

CROSS-REFERENCES TO RELATED APPLICATIONS

This application is a continuation of application Ser. No. 09/400,438 filed on Sep. 21, 1999, which is a continuation of application Ser. No. 09/088,849 filed on Jun. 2, 1998, now U.S. Pat. No. 5,954,932, which is a continuation of application Ser. No. 08/669,915 filed on Jun. 25, 1996, now U.S. Pat. No. 5,759,374, which is a continuation of application Ser. No. 08/337,412 filed on Nov. 7, 1994, now U.S. Pat. No. 5,529,679, which is a continuation of application Ser. No. 08/051,324 filed on Apr. 23, 1993, now abandoned, which is a continuation-in-part of application Ser. No. 08/026,592 filed on Mar. 5, 1993, now U.S. Pat. No. 5,314,602, which is a continuation of application Ser. No. 07/843,232 filed on Feb. 28, 1992, now U.S. Pat. No. 5,268,080, which is based on Japanese application No. 3-34006 filed on Feb. 28, 1991. The disclosures of application Ser. Nos. 08/026,592 and 07/843,232 are hereby incorporated by reference.

BACKGROUND OF THE INVENTION

The present invention relates to a method of detection of DNA and protein and of DNA base sequencing determination and to an apparatus therefor.

It relates more particularly to the fluorescence detection type gel electrophoresis apparatus.

For DNA base sequencing determination by electrophoresis gel separation, a radioisotope label has been used as a label for a DNA fragment. Due to the inconvenience of this method, however, a method of using a fluorescence label has come to be increasingly employed. (Refer to U.S. patent application Ser. No. 07/506,986 (U.S. Pat. No. 5,062,942) and Bio/Technology Vol 6, July 1988, pp816–821, for example.) As an excitation light source this method uses an argon laser with an output of 20 to 50 mw and a wavelength of 488 nm or 515 nm to detect the DNA fragment of $10^{-16}$ mole/band to $2 \times 10^{-18}$ mole/band. As fluorophores, the method has used FITC (fluorescein isothiocyanate with a maximum emission wavelength of 515 nm), SF (succinyl fluorescein with a maximum emission wavelength of 510 nm to 540 nm), TRITC (tetrarhodamine isothiocyanate with a maximum emission wavelength of 580 nm) and Texas Red (sulforhodamine 101: a maximum emission wavelength of 615 nm).

Normally, electrophoresis is performed with polyacrylamide gel placed on the plate which is provided between two glass plates. In recent years the capillary gel eleclrophoresis method has been developed, where gel is formed in the capillary. Use of a capillary having a smaller diameter increases the surface area per volume of gel; this feature facilities the dissipation of Joule heat, permitting application of high voltage. A high-speed electrophoresis separation is provided by the capillary gel electrophoresis method.

The first example of the capillary gel electrophoresis method as a prior art is described in Nucleic Acid Research, Vol. 18. pp. 1415 to 1419 (1990), Journal of Chromatography, Vol. 516, pp. 61–67 (1990), and Science, Vol. 242, pp. 562–564 (1988). Another method of using one migration lane for base sequence determination is disclosed in Nature Vol. 321, pp. 674–679 (1986) and others.

The above-mentioned conventional technique, however, has disadvantages in that the sensitivity is insufficient, and the entire equipment must be made greater in size because the Ar laser is greater in size than a He—Ne laser.

SUMMARY OF INVENTION

The first object of the present invention is to provide a solution to the above-said problems and to provide a method and small-sized device in which extra-sensitive DNA detection is made possible. To achieve the object, the present invention uses a He—Ne laser with an emission wavelength of 594 nm in DNA base sequencing determination by fluorescence detection type eleclrophoresis gel separation, and adopts a highly efficient photodetecting system.

The said examples of the prior art use one capillary, but sufficient consideration has not been given to simultaneous processing of two or more samples. In the capillary electrophoresis apparatus, the decreasing size of the samples requires higher detection sensitivity and simultaneous processing of two or more samples. For fluorescence detection in the state of electrophoresis, generally, the background from the gel, scattered light from the inner and outer walls of the capillary as the gel support or fluorescence from the capillary itself is produced in addition to the fluorescence from the object fluorophore itself, resulting in higher background level and reduced detection sensitivity. One of the major problems in ensuring highly sensitive fluorescence detection is how to cut off such backgrounds. Improvement of processing capabilities and simultaneous processing of two or more samples require an increase in migration speed, or detection by migration of the DNA fragments through simultaneous use of two or more capillaries which are migration lanes. In practice, there remains a problem of how to cut off the background to achieve highly sensitive fluorescence detection, as mentioned above.

The second object of the present invention is to solve said problems to provide a capillary electrophoresis apparatus and its method which ensure fluorescence detection of two or more samples, and high-speed highly sensitive DNA detection.

The measuring limit for the DNA fragment labeled by a fluorophore in the process of electrophoresis gel migration is determined by the intensity and fluctuation of the background fluorescence from the gel with respect to fluorescence for labeling. The background fluorescence from the gel is gradually reduced with the increase of the emission wavelength.

Thus, the excited at the optimum wavelength, the quantity of the fluorescence normalized by the background fluorescence from the gel is the greatest in the case of Texas Red (sulforhodamine 101). According to this normalized quantity of the fluorescence, the sensitivity of the Texas Red is five to ten times that of FITC. In the present invention, there has been used Texas Red or its derivative as a labeling fluorophore, and a He—Ne laser with the wavelength of 594 nm, which is close to the optimum wavelength, as the excitation light source. The wavelength of 594 nm for the excitation light is close to the maximum emission wavelength of the Texas Red which is 615 nm. One of the problems was how to remove the scattered light from the excitation light, and the present invention has succeeded in removing this scattered light by using a sharp-cutting fluorophore filter which will be described below. The output from the He—Ne laser with the wavelength of 594 nm ranges from 1 mw to 7 mw. The output from a typical model of the He—Ne laser (594 nm) is as small as 2 mw, and greater emission strength cannot be obtained; therefore, the detecting sensitivity greatly depends on the fluctuation of the background fluorescence from the gel. To solve this problem, the present invention has improved the photodetecting system, and has adopted a photodetecting system which receives a greater amount of light by two or more digits than the excitation light scanning method. Namely, the excitation light is made to be incident upon the gel plate through the side thereof, and the entire measured area is irradiated simultaneously to increase the overall emission strength. Furthermore, a cylindrical lens is used to increase the photodetecting solid angle.

Changing the wavelength of the excitation light from 488 nm to 594 nm has reduced the background fluorescence from the gel down to approximately one fifth when the laser of the same output is used. In addition, when the conventional argon laser (about 20 mw) is employed, FITC is subjected to photodestruction, and this results in reduced emission strength, and hence reduced sensitivity. By contrast, under the 2.5 mw He—Ne laser irradiation, photodestruction of the fluorophore hardly occurs to the Texas Red during measurement. This permits the emission strength normalized by the background fluorescence from the gel to be greater by one digit than that of FITC.

In the laser scanning method, the area of 100 mm is swept by the laser beam of approximately 0.3 mm in diameter. Even when the conventional 50 mw laser is used, the average laser intensity with which each point is irradiated is as small as 17 microwatts, since the irradiation time at each point is reduced. When the 2.5 mw laser is used, the average laser intensity is approximately 0.9 microwatts, and this almost cannot be put into practical use. The irradiation intensity is 2.5 mw in the lateral incidence method employed in one of the present embodiments, and this emission is sufficient. However, in the scanning method the photodetecting efficiency can be made approximately 2 percent, but in the simultaneous irradiation method, the fluorescent image is received in a reduced size; therefore the photodetecting efficiency is reduced to 0.1 percent or less.

Defining a solid angle as $\Omega$ and the transmittance of the filter or the like as T, the photodetecting efficiency $\eta$ can be expressed by the following formula (1):

$$\eta = \frac{\Omega T}{4\pi} \quad (1)$$

Assuming the image reduction ratio as m and the f-number of the lens as F, $\Omega$ is represented as:

$$\Omega = \frac{\pi}{4(m+1)^2 F^2} \quad (2)$$

Thus, the photodetecting efficiency $\eta$ can be expressed by the following formula (3):

$$\eta = \frac{1}{16(m+1)^2 F^2} \quad (3)$$

where m represents (length of the measured portion)/(length of the detector). In the scanning method, m<1; and in the lateral incident method, 120 cm/24 cm<m<120 cm/18 cm by way of an example, namely m is approximately from 5 to 7. Accordingly, the photodetecting rate of the lateral incident method is approximately 1/50, because of the term of $(m+1)^2$ in formula (3), on the one hand. On the other hand, in the case of the scanning method where light is not continuously received from each measured point, the result is multiplied by 3/1000 to 5/1000 as a factor due to duty cycle. Thus, in total, the lateral incident method yields a greater photodetecting efficiency than the scanning method. When the laser having a smaller output such as a He—Ne laser is used, it is important to find a means to obtain a sufficient photodetecting efficiency. The present invention uses the cylindrical lens to increase the photodetecting efficiency by, for example, four to five times. This system provides a high photodetecting efficiency, ensuring highly sensitive detection of the fluorescent image.

U.S. patent application Ser. No. 07/506,986 discloses the case of using Texas Red and the He—Ne laser having a wavelength of 543 nm. (Compared With the case of using the 594 nm He—Ne laser, the excitation efficiency is as low as 1/3, and the output is also as low as 1 mw.

To achieve the second object, in the electrophoresis apparatus wherein samples DNA fragments, etc. labeled by the fluorophore are subjected to separation by electrophoresis, providing optical detection and analysis of the separated samples, an optical detecting portion for sample detection, for which the electrophoresis separation region provided between the vessel for cathode electrode and vessel for anode electrode is composed of capillaries, has the following configurations:

In the configuration (1) of said optical detecting portion; the ends of said one pair or more pairs of capillaries are connected to said vessel for cathode or anode electrode, and the other ends are held at a specified gap, with their axes almost matched to each other, and are laid face to face with each other in the optical cell to form a migration lane which passes through said optical cell; sheath solution is supplied into said optical cell from the outside; the sample migrated from the capillary end of the upstream migration lane, namely, the sample separation region, is put in the sheath flow condition, and is then lead into the downstream capillaries laid out face to face; while said gap is used as an optical detecting portion, and light from the light source is shed on this optical detecting portion, thereby detecting the samples. In this configuration (1), two or more detecting portions formed by ttwo or more pairs of capillaries are laid out in the optical cell. Furthermore, two or more pairs of capillaries are arranged in the optical cell so that two or more detectors formed by two or more pairs of capillaries are located in a straight line, and the excitation light is shed along said straight line so that all the optical detecting portions are simultaneously irradiated, thereby ensuring simultaneous detection of the fluorescence at said two or more optical detecting portions.

In the configuration (2) of the optical detecting portion; two or more capillaries, the other ends of which are immersed in the electrode vessel, are terminated in the optical cell, and sheath solution is supplied into said optical cell from the outside. Thus, the samples migrating from capillaries are made to flow in the optical cell in the sheath flow condition. Using the sheath flow region as the optical detecting portion, light is irradiated on the optical detecting portion, thereby detecting the samples. In this configuration (2), two or more capillaries are laid out in the optical cell so that two or more optical detecting portions are located in a straight line, and the excitation light is shed alone said straight line so that all the optical detecting portions are simultaneously irradiated, thereby ensuring simultaneous detection of the fluorescences issued from the samples migrating from capillaries.

In configurations (1) and (2), the following configuration is also possible:

The sample separation region is composed of the capillary gel, and the sheath solution has the same components as those of the buffer solution inside the capillaries. The denaturant for the sample may be contained as required. The sheath solution level is positioned higher than the liquid level in the downstream electrode vessel, and the sheath solution is made to flow by the head of two liquids.

In the configuration (3) of the optical detecting portion; two or more capillaries, the other ends of which are immersed in the electrode vessel, are terminated in the optical cell filled with electrolyte. The optical detecting portion belongs to the region close to the terminal to which the samples migrate from the capillary gel as migration lane. The optical detecting portion filled with electrolyte is formed as follows: two capillaries are laid out in a straight line with their axes almost matched to each other, and the ends laid face to face with each other are placed in close contact with each other in the axial direction of the capillary, while maintaininq a specified gap. In this case, samples are subjected to electrophoresis separation inside one of the capillaries located in the upstream side of the migration lane, while the gap serves as optical detecting portion to detect the fluorescence emitted by samples. The gap length is preferred to be 1 mm or less. The two or more optical detecting portions formed by two or more pairs of capillaries are linked with each other by the electrolyte. Two or more optical detecting portions are arranged in a straiqht line, and a single excitation light is shed along this straight line, ensuring simultaneous detection of the fluorescences issued from the two or more samples.

In the electrophoresis apparatus provided with optical detecting portion according to said configuration (1), sheath solution is supplied into the optical cell from the outside, so samples migrating from the capillary end in the migration lane on the upstream side where the samples are separated can be led to the capillaries facing each other in the sheath flow condition, and samples migrate continuously in capillaries on the upstream side and those on the downstream side. Furthermore, the samples migrate smoothly in the gap on the axis between the capillaries on the upstream side and those on the downstreamn sides. This gap is used as the optical detecting portion. Liqht can be irradiated on the optical detecting portion in the sheath solution containing no capillaries, detecting the samples by fluorescence. This eliminates the possibility of backgrounds being emitted from capillaries or capillary gels, ensuring highly sensitive fluorescence detection. It allows use of the rectangular optical cell which can be manufactured easily at lower cost. Two or more optical detectors can be arranged in close proximity with each other in the optical cell, resulting in substantial reduction of the system size. Samples migrating from the capillaries are put into sheath flow condition for each capillary when passing through the optical detecting portion, and sheath flow is all put under the same conditions. Sheath flow conditions such as flow speed are made uniform for each capillary, resulting in improved accuracy in optical detection of samples. Two or more optical detecting portions are arranged in a straight line in one optical cell, and excitation light is irradiated along this straight line, permitting simultaneous irradiation of all optical detecting portions and simultaneous fluorescence detection by two or more optical detectinq portions. Furthermore, two or more optical detecting portions are linked with each other through the solution, so the excitation right is not bent by capillaries, and the excitation light intensity is not damped. This allows irradiation of the optical detecting portions with sufficient light intensity, providing high-precision highly sensitive fluorescence detection. Use of the two-dimensional TV camera, etc. for light detector permits simultaneous photodetection of the fluorescent images of two or more optical detecting portions. Two or more optical detecting portions can be positioned in close proximity with each other in a straight line, and the length between the optical detecting portions on the extreme ends of this straight line can be reduced, permitting configuration of the smaller apparatus. Reduced distance between optical detecting portions located on the extreme ends will allow all optical detecting portions to be irradiated in almost the same light beam diameter, even when the excitation light is condensed by the lens or the like.

For example, when the laser light is condensed to 100 $\mu$m in terms of the focal point, the laser light diameter will be about 100 $\mu$m over the range of about 10 mm on the front and rear of the focal point. When capillaries having an outer diameter of 200 $\mu$m and inner diameter of 100 $\mu$m are arranged at the intervals of 400 $\mu$m, about 50 capillaries can be installed within the range of about 10 mm on the front and rear of the focal point, and they can be irradiated with the equivalent light beam diameter and intensity. This allows the optical detecting portions to be irradiated with the excitation light condensed, and the fluorescence intensity to be increased, thereby ensuring highly sensitive detection of the sample.

Moreover, it is also possible to make the downstream capillaries hollow (i.e. open capillaries), allowing effective flowing of the sheath solution. In addition to the capillaries, it is also possible to use on the downstream side something that performs the equivalent operations, for example, the plate provided with holes and grooves in the same number as that of the upstream capillaries. The flow of electricity at the gap (namely, the optical detecting portion) can be ensured by making the sheath solution have the equivalent components as that of the buffer solution within the capillary, thereby providing electrophoresis of samples. Furthermore, because the buffer solution has the same components both inside and outside the capillary, there is no possibility of the buffer solution inside the capillary flowing out into the optical cell causing their composition to be changed. Therefore, the sample separation function in electrophoresis is not lost. When the samples are single-strand DNAs, denaturant can be contained in the sheath solution, and it is possible to avoid rebonding when DNA samples migrates in the gap (namely, the optical detecting portion); this means improved detection accuracy. This feature reduces the possibility of the denaturant contained in the capillary leaking out into the optical cell, and eliminates the loss of sample separation function.

The gap length is preferred to be 0.1 mm to 3.0 mm. Generally, the smaller gap length provides easier electrophoresis of the samples in the gap space, so the space distance should be short. However, assembling of the apparatus is more difficult if the gap length is very small; therefore, it is preferred to be 0.1 mm or more in practice. However, it can be set to 0.1 mm or less. The limit is determined by the size of the excitation beam such as laser light at the gap. Conversely, greater gap length will cause easier dispersion of the samples. The gap length of about 3.0 mm allows normal electrophoresis of the samples on the line connecting between capillaries.

In the electrophoresis apparatus provided with optical detecting portion according to said configuration (2), samples migrating in the capillaries flow in the optical cell in the sheath flow state. By using the sheath flow region as optical detecting portion and the same configuration as that of (1), it is also possible to detect separately the samples migrating in the capillaries, thereby obtaining the same results as configuration (1). The layout of the optical detecting portion and irradiation of the excitation light discussed in connection with the configuration (1) are the same for configuration (2).

In the configuration (3) of the electrophoresis apparatus; samples are detected in the electrolyte without containing any gel, eliminating the possibility of backgrounds being emitted from gel supports such as the capillaries, ensuring highly sensitive fluorescence detection. Moreover, it eliminates the need of making the electrolyte, and provides simple configuration of the apparatus. The sap is used as optical detecting portion to detect the fluorescence of samples; it is also filled with electrolyte, permitting electrophoresis. Since gel is produced in at least one of the capillaries, formation of the migration lane is facilitated. The preferred gap length is 0.1 mm to 1 mm. Generally, the smaller gap length provides easier electrophoresis of the samples in the gap space, so the space distance should be short. However, assembling of the apparatus is more difficult if the gap length is very small; therefore, it is preferred to be 0.1 mm or more in practice. However, it can be set to 0.1 mm or less. The limit is determined by the size of the excitation beam such as laser light at the gap.

Conversely, greater gap length will cause easier dispersion of the samples without migrating in a straight line in the gap; samples will not migrate in the others of the paired capillaries. The gap length of about 2 to 3 mm allows normal eleclrophoresis of the samples; however, normal eleclrophoresis may take place, depending on the conditions such as electrophoresis voltage. The gap length of about 1 mm is preferred in practice. That is, the gap length of 0.1 mm to 1.0 mm allows smooth and effective eleclrophoresis of the samples. Two or more optical detecting portions can be positioned in a straight line, and a single excitation light can be irradiated simultaneously on two or more optical (detecting portions for fluorescence detection. Furthermore, two or more optical detecting portions are linked with each other through the solution, so the excitation light is not damped. This allows irradiation of the optical detecting portions with sufficient light intensity, providing high-precision highly sensitive fluorescence detection.

To summarize the present invention, one or more samples are subjected to electrophoresis separation using the plate gel and capillary gel, and two or more migration lanes are irradiated linearly by the laser from the direction which is almost perpendicular to the migration direction for samples and which is parallel to the surface formed by two or more migration lanes, thereby providing real-time detection of the fluorescence emitted from the fragments migrating in the migration lane. The present invention relates especially to the fluorescence detection type electrophoresis apparatus provided with the optical cell which is intended for highly sensitive fluorescence detection of the DNA fragments labeled by fluorophores, wherein one pair or more pairs of capillary filled with gel and capillary are arranged in the optical cell so that they are coaxial with each other and a specified gap length is maintained. The sheath solution is poured into the optical head by the cell and the samples migrating in the gap are put in the sheath flow condition. Fluorescence detection is performed in the gap free of capillary or gel. Or the buffer solution is poured in the optical cell, and the gap is filled with buffer solution, thereby forming the migration lane through the gap, which is used for fluorescence detection. Using sulforhodamine 101 or rhodamine derivative as fluorophore, He—Ne laser light having an emission wavelength of 594 nm is irradiated along the straight line in which two or more gaps are arranged; then the fluorophore is excited to permit fluorescence detection. Since the fluorescence detection is performed in the gap free of capillary or gel, it is possible to obtain a small type electrophoresis apparatus which provides simultaneous electrophoresis of two or more samples and their simultaneous detection, thereby ensuring highly sensitive fluorescence detection, free from background influence.

DESCRIPTION OF THE PREFERRED EMBODIMENTS

The following gives detailed description of the present invention with reference to embodiments:

[EMBODIMENT 1]

Figure 1:
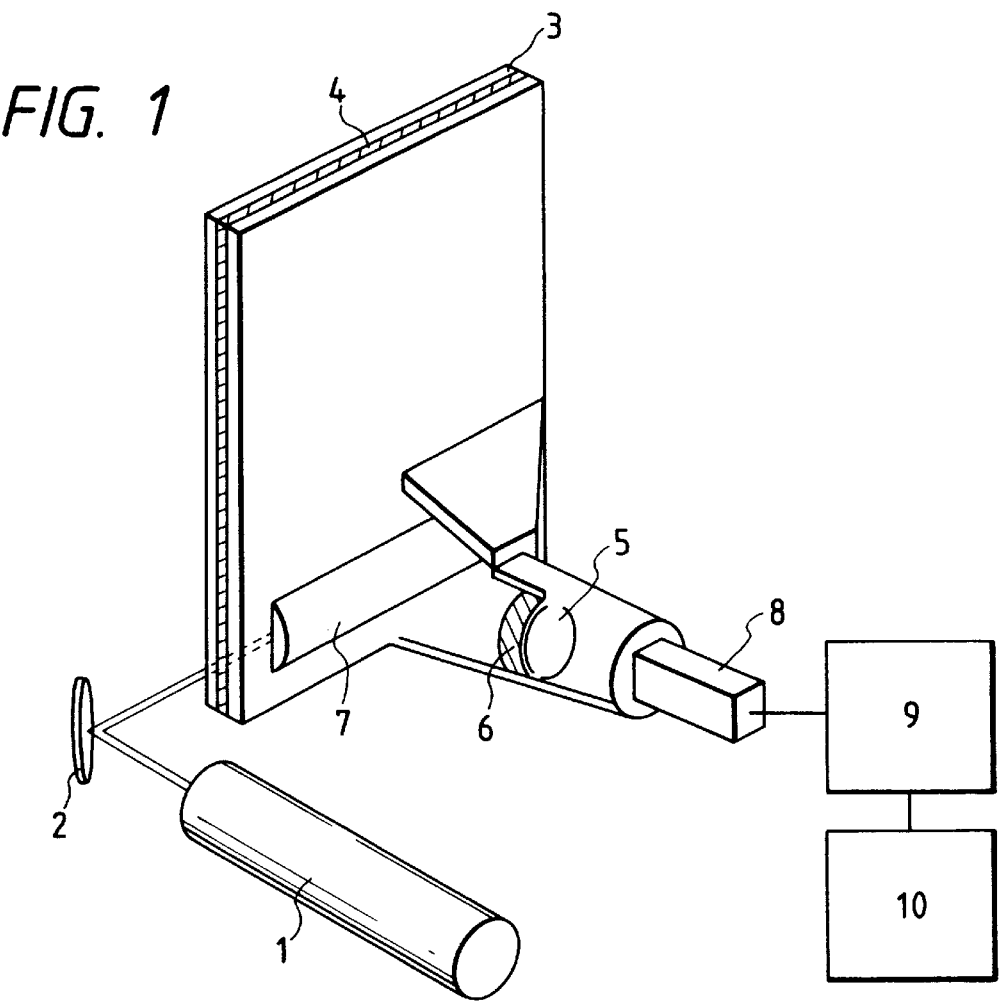
FIG. 1 is a schematic view representing the DNA detector as the first embodiment of the present invention.

First embodiment of the present invention will be described with reference to FIGS. 1 and 2. FIG. 1 is a schematic view representing the detector. Light emitted from the 594 nm He—Ne laser 1 irradiates the electrophoresis separation gel plate 4 from the side. After being collected by the cylindrical lens 7, the fluorescence emitted from the linearly irradiated portion is filtered out by the band pass filter 6, and forms images on the line sensor or secondary detector 8 through the lens for image formation 5. Filter 6 is a 6-cavity multilayer interference filter with a diameter of 50 mm, and transmittances for light having wavelengths of 594 nm, 600 nm, 610–630 nm and 640 nm are $10^{-4}$, $10^{-2}$, 0.6 or more, and 0.01 or less, respectively.

The concentration of the acrylamide gel constituting the gel plate 4 (concentration of the total quantity of monomer)

is 4 to 6 percent (g/cc). When irradiated by the He—Ne laser with the wavelength of 594 nm, the background fluorescence from the gel has the same intensity as the fluorescence from Texas Red having a concentration of $2 \times 10^{-11}$ mole. The laser power is 2.5 mw and the beam diameter is 0.3 mm. The positional resolution on the linearly irradiated portion of 0.5 mm is sufficient. In FIG. 1, the reference numeral 2 denotes a reflection mirror, 3 a glass plate sandwiching the gel plate 4 sandwiched, 9 a control circuit, and 10 a data processor. The number of the photons I of the fluorescence emitted from the 0.5 mm-long area irradiated by the laser beam can be obtained from the following formula:

$$I \sim I_0 \cdot \phi \cdot [I - e^{-\epsilon l M}] \sim I_0 \phi \epsilon l M \quad (4)$$

where $I_0$ denotes the number of incident photons, $\phi$ denotes a quantum yield of the fluorophore, $\epsilon$ denotes a molar absorption coefficient, l denotes a optical path length and M denotes a mole concentration of the fluorophore. The number of the photons emitted from the 2.5 mw laser per second (namely, $I_0$) is approximately $10^{16}$. When Texas Red of approximately 0.4 in $\phi$ is irradiated with the light having the wavelength of 594 nm, the absorption coefficient of Texas Red $\epsilon$ is approx. $8 \times 10^4$ cm$^{-1}$(M)$^{-1}$, l is approx. 0.05 cm, and the concentration M of Texas Red showing the same level of fluorescence as that of the gel is approx. $2 \times 10^{-11}$ moles/l. The number of photons I from Texas Red which emits the same amount of the fluorescence as that of background fluorescence from the gel is estimated to be approximately $3 \times 10^8$ per second.

When a 10 cm area is scanned by the laser beam, the duty cycle is 0.5/100. Therefore, the average number of photons emitted from the 0.5 mm-long area is $1.5 \times 10^6$ per second. Even when the lens having a greater F-value is used to receive light, the photodetecting efficiency is 1 to 2 percent when consideration is given to the filter transmittance (approximately 50%). When consideration is given to the quantum yield (approximately 5%) on the photodetecting surface, the number of photons to be received is 1000 per second or less. Thus, the scanning method fails to Provide high-precision measurement.

In the lateral incident method proposed in the present invention, however, the duty cycle is 1.0, but since the reduced image is formed on the detector, the photodetecting efficiency is as small as approx. 0.05%. The number of protons emitted from the 0.5 mm-long area which enter the detector is approx. $7.5 \times 10^3$ per second when the quantum efficiency on the photodetecting surface and losses due to various factors are taken into consideration. The detection sensitivity is determined by the fluctuation of the background fluorescence to be measured.

In this case, the statistical fluctuation is approximately ±1.2 percent. Generally, the relative value of the fluctuation is reduced with the increase of the photodetecting quantity, and even a slight signal can be measured. If the photodetecting quantity is increased by N times, the relative fluctuation is reduced to $\pm 1/\sqrt{N}$. For example, when the photodetecting quantity is increased by four times, the relative fluctuation is reduced by one half. To ensure highly sensitive detection, the above-said fluctuation of approx. ±1.2% must be further reduced, and the photodetecting quantity must be increased.

To realize this, the present invention uses a cylindrical convex lens (focal distance f=25 mm, f-number F=1.0) which is installed at a position approximately 25 mm away from the irradiation section, and a cylindrical concave lens (f=−200 mm) which is placed immediately before the lens for image formation so that the image in the vertical direction will be formed in an enlarged size; hence the photodetecting solid angle has been increased four to five times. This has increased the photodetecting quantity by four to five times, and has reduced fluctuation by half down to approximately ±0.6% of the fluorescence emitted from the gel, thereby ensuring a highly sensitive detection capability. Namely, this detection system permits detection of Texas Red of $2 \times 10^{-13}$ moles/l at an S/N ratio of approximately 1.

When the argon laser is used as an excitation light source, and Texas Red is used as a labeling fluorophore, the excitation efficiency is reduced by one digit compared with that of the present embodiment, and the sensitivity is also reduced undesirably by one digit. When the argon laser is used as an excitation light source, and FITC is used as a labeling fluorophore, the background fluorescence is increased by one digit compared with that of the present embodiment, and the labeling fluorophore is subjected to photodestruction during the measurement so that the effective FITC concentration is reduced. As a result, the sensitivity is also reduced undesirably by two digits compared with that of the present embodiment.

Figure 2:
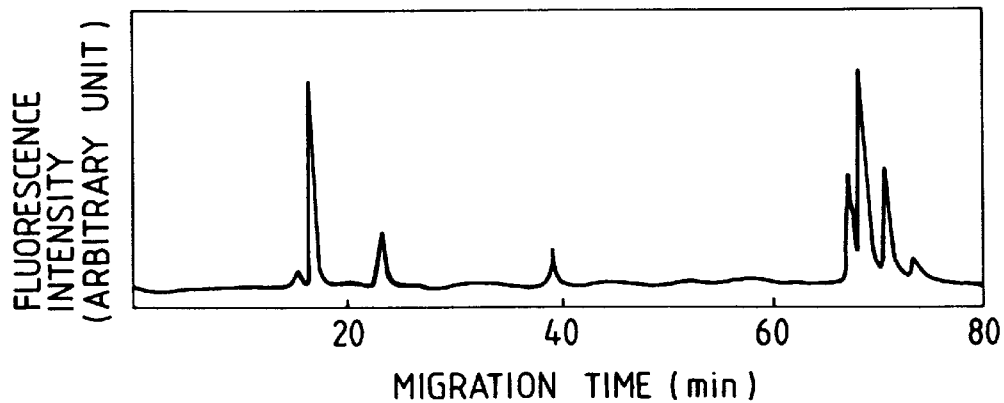
FIG. 2 is a graph representing the spectrum in the electrophoresis separation of the DNA fragment which is obtained by letting the λ phage be digested by the restriction enzyme and by inserting the fluorescence label into the cut portion.

FIG. 2 represents an electrophoresis separation pattern of the fragment which is digested by the enzyme wherein the terminal of the λ phage is labeled by Texas Red and the He—Ne laser of 594 nm wavelength is employed. The cubic volume of the DNA band is estimated at 1 μl, and it is possible to read the signal from the sample which is injected $2 \times 10^{-19}$ moles.

By contrast, the quantity of the sample for which the signal can be read is $1 \times 10^{-17}$ moles per band in the conventional case of using FITC and the argon laser, and is $2 \times 10^{-18}$ moles per band in the conventional case of using Texas Red and the argon laser.

The following Table shows the comparison between an example of the He—Ne laser used in the present invention and an example of the argon laser used in the conventional case. This reveals that the He—Ne laser is smaller in size, lighter in weight and usually less costly than the argon laser.

|  | He—Ne-laser | | Argon laser | |
| --- | --- | --- | --- | --- |
|  | Size (cm) | Weight (kg) | Size (cm) | Weight (kg) |
| Power supply | 8 × 15 × 15 | 2 | 15 × 40 × 30 | 20 |
| Resonator | 7 (dia.) × 4 | 2 | 15 × 15 × 35 | 10 |

Thus, the DNA detector of the present invention features not only a higher sensitivity but also a smaller size than the conventional device.

As described above, according to the present invention, Texas Red or rhodamine derivatives having an emission band in the long wave area of less background fluorescence from the gel can be effectively excited by the yellow He—Ne laser with the wavelength of 594 nm, so that this characteristic ensures a higher sensitivity and a smaller configuration.

[EMBODIMENT 2]

In the present Embodiment, DNA fragments labeled by fluorescence are separated by electrophoresis and detection is made by fluorescence. The following describes the case of using Texas Red (Sulforhodamine 101, maximum emission wavelength of 615 nm) as labeling fluorophore. The DNA fragments as samples are labeled by fluorophores. DNA fragments labeled by fluorophores are prepared by DNA polymerase reaction, using the primer labeled by fluorophore according to the well-known dideoxy sequencing method invented by Sanger and his colleagues. The details of the method of preparing samples according to Sanger's dideoxy sequencing method are described in the Embodiment 3.

Figure 3:
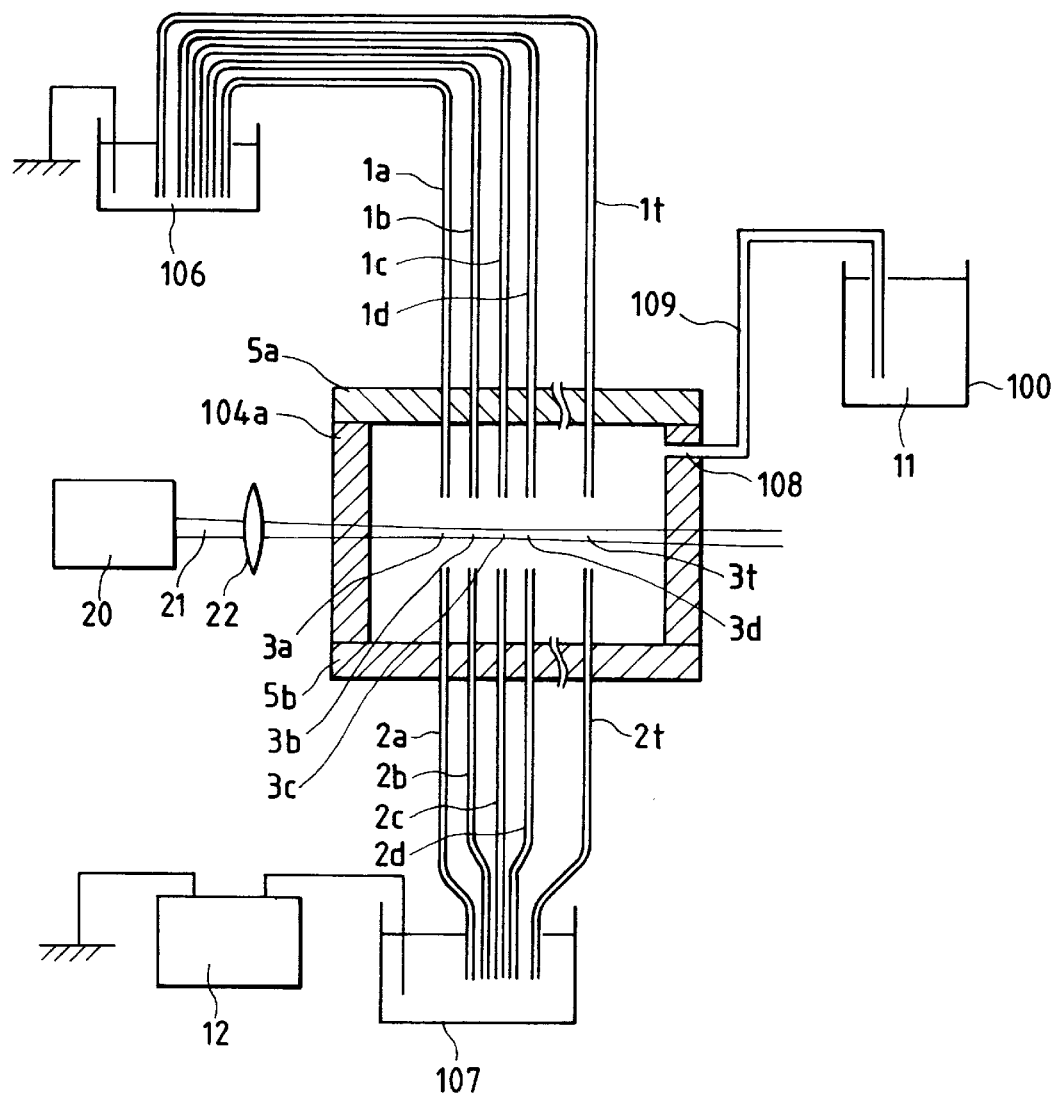
FIG. 3 is a lock diagram representing the electrophoresis region and laser irradiation system of the elecurophoresis apparatus according to the second Embodiment of the present invention.
Figure 4:
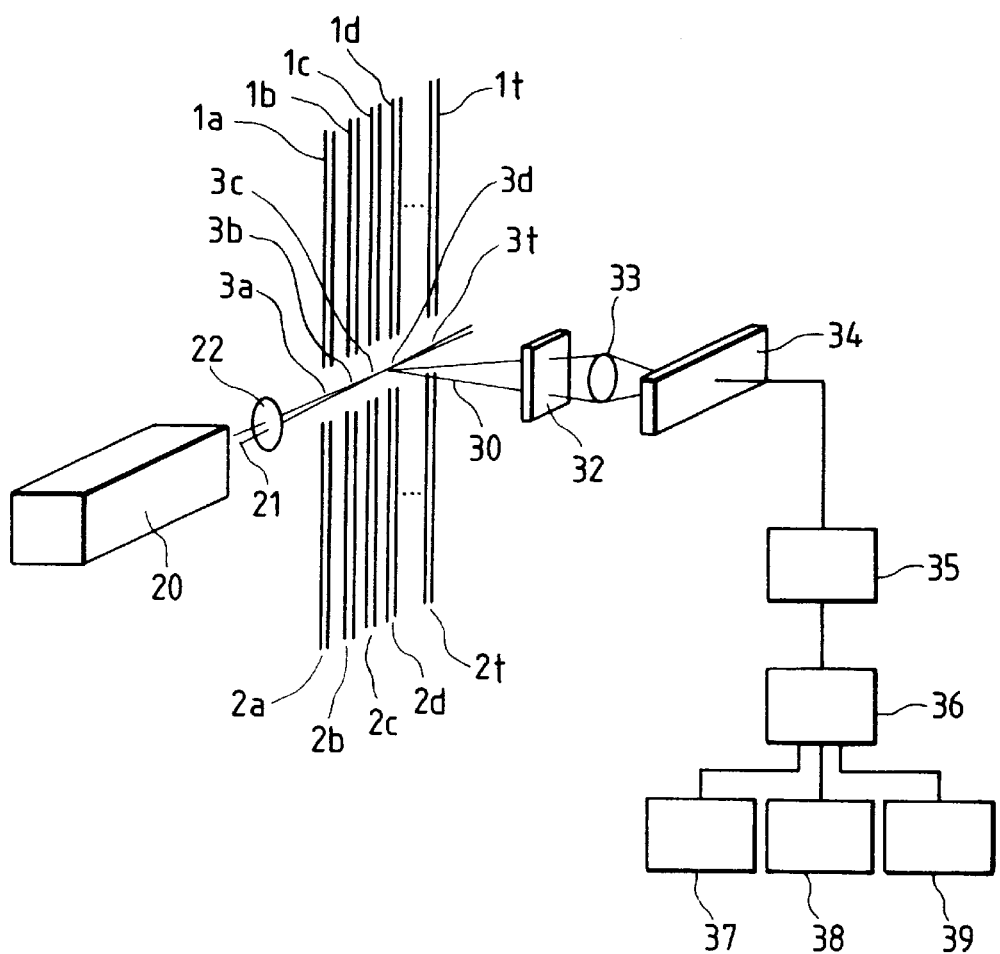
FIG. 4 is a block diagram representing the fluorescence detection system of the electrophoresis apparatus according to the second Embodiment of the present invention.

Firstly, the apparatus configuration will be described. FIG. 3 shows the electrophoresis region and laser irradiation system of the electrophoresis apparatus according to the present Embodiment. FIG. 4 represents the fluorescence detection system of the electrophoresis apparatus. The electrophoresis apparatus includes an arrangement of 20 capillaries serving as the electrophoresis region to perform simultaneous detection of two or more samples. The electrophoresis separation region uses 20 silica-made capillaries 1a, 1b, 1c, 1d . . . 1t, all having the same form; an inner diameter of 100 μm, outer diameter of 375 μm and length of 40 cm, as well as 20 silica-made capillaries 2a, 2b, 2c, 2d . . . 2t, having the same inner and outer diameters but a length of 10 cm.

The capillary gel is produced by filling capillaries 1a to 1t with polyacrylamide gel containing the denaturant urea. Firstly, the capillary interior is washed and is subjected to silane coupling treatment. Then solution of N,N,N',N'-tetramethylethylendiamine and ammonium persulfate is added to the degassed TRIS-borate buffer containing 3.84 percent of acrylamide, 0.16 percent of N,N'-methylene bis-acrylamide, 7 M of urea, and 2 mM of EDTA, and is poured into the capillaries; then polyacrylamide gel is obtained by polymerization. Polyacrylamide gel and capillaries are chemically bonded with each other, and the gel does not come out of the capillaries (luring electrophoresis.

Capillaries 2a to 2t are treated so that their inner surfaces are positively charged. Firstly, 3-(2-aminoethylaminopropyl) trimethoxysilan solution is poured into capillaries to cause reaction. It is then heat treated at the temperature of 110° C., and amino acid residue is introduced on the inner walls of the capillaries to be positively charged. This changes the direction of the electroosmotic flow from negative to positive poles inside each of capillaries 2a to 2t.

The migration direction (from negative to positive poles) of samples in capillaries 1a to 1t filled with polyacrylamide gel is matched to the migration direction (from negative to positive poles) of samples in capillaries 2a to 2t, ensuring the sample migration. The ends of capillaries 1a to 1t and capillaries 2a to 2t are placed face to face in the optical cell, and are held at a specified gap; then samples migrating in these gaps are detected optically. According to the present invention, the fluorescent cell is used to detect the samples by fluorescence. That is, the ends of said capillaries la to it and capillaries 2a to 2t are placed inside the rectangular quartz optical cell 104a (outer dimensions: 36 mm wide by 4.5 mm deep by 3 mm long; inner dimensions: 30 mm wide by 2 mm deep by 3 mm long); where width denotes the horizontal direction of the drawing (direction of capillaries 1a→1t), the depth the perpendicular direction of the drawing, and the length the longitudinal direction (direction of samples migrating in capillaries) of the drawing. They are arranged so that a pair of capillary 1a and capillary 2a will be coaxial with each other, and that they will face each other forming the gap 3a having a length of 1 mm. Likewise, capillaries 1b and 2b, 1c and 2c, 1d and 2d . . . 1t and 2t are arranged so as to form gaps 3b, 3c, 3d . . . 3t. Gaps 3b, 3c, 3d . . . , 3t are arranged in a straight line at a specified interval. To hold the capillaries in the optical cell, use is generally made of the multi-capillary holder having 20 vertical holes at intervals of 0.6 mm provided on the plate-formed block made of fluorine-contained polymer, for example, tetrafluoroethylene polymer. Namely, each of capillaries 1a to 1t is inserted in each of 20 vertical holes of multi-capillary holder 5a; then each of capillaries 2a to 2t is inserted in each of 20 vertical holes of multi-capillary holder 5b. The multi-capillary holder 5a and multi-capillary holder 5b are fixed in close contact with the top and bottom of optical cell 104a to ensure that capillaries 1a and 2a, 1b and 2b, 1c and 2c, 1d and 2d . . . 1t and 2 are respectively coaxial.

Furthermore, since the gaps 3a to 3t are used as optical detecting portions, adjustment is made of the length of capillaries 1a to 1t and 2a to 2t inside the optical cell 104a so that gaps 3a to 3t are laid out in a straight line. The other ends of the capillaries 1a to 1t and 2a to 2t are immersed in a vessel for cathode electrode 106 and a vessel for anode electrode 107 supplied with buffer solution (TRIS-borate-EDTA buffer solution with urea). The inside of optical cell 104a is provided with sheath inlet 108 to be filled with sheath solution, so that sheath solution 11 in the sheath solution bottle 100 can be supplied through the tetrafluoro-ethylene polymer tube 109. Sheath solution 11 uses the TRIS-borate-EDTA buffer solution with urea, having the same composition as that of the buffer solution inside the capillary gel of capillaries 1a to 1t, thereby preventing the components of the capillary gel from leaking into the optical cell 104a.

Furthermore, if optical cell 104a incorporating capillaries 1a to 1t and capillaries 2a to 2t is filled with sheath solution and the level of sheath solution 11 of sheath solution bottle 100 is made higher than that of the buffer solution in the vessel for anode electrode 107, then sheath solution flows into the vessel for anode electrode 107 through capillaries 2a to 2t. Under this condition, optical cell 104a and capillaries 2a to 2t are filled with sheath solution, namely, buffer solution, and capillaries 1a to 1t are also filled with capillary gel. If the DC voltage is applied between the vessel for cathode electrode 106 and the vessel for anode electrode 107 by DC high voltage power supply 12, then current will flow through capillary 1a, gap 3a and capillary 2a, allowing the samples to migrate. When the level of sheath solution 11 of sheath solution bottle 100 is made higher than that of the buffer solution in the vessel for anode electrode 107, sheath solution flows inside the capillaries 2a to 2t, producing the flow over the tops of the capillaries 2a to 2t, namely, around gaps 3a to 3t. Samples migrating from capillaries 1a to 1t pass through gaps 3a to 3t along the flow over capillaries 2a to 2t under the sheath flow conditions, are led into each capillary and made to migrate toward the vessel for anode electrode 107.

Capillaries 2a to 2t are treated so that their inside will be positively charged, and electroosmotic flow inside the capillaries 2a to 2t is directed from capillaries 1a to 1t vessel for anode electrode 107, eliminating the possibility of reserve flow of the solution into gaps, and ensuring stable flow of sheath solution toward the vessel for anode electrode 107. Even when the flow rate of sheath solution is especially low, stable flow of sheath solution toward the vessel for anode electrode 107 is ensured.

Electrophoresis is performed by application of DC power between the vessel for cathode electrode 106 and the vessel for anode electrode 107 by means of DC high voltage power supply 12. The current flowing through capillary 1a and capillary 2a goes mainly through gap 3a; likewise, the current flowing through capillaries 1b and 2b, 1c and 2c, 1d and 2d, . . . 1t and 2t goes mainly through 3b, 3c, 3d . . . 3t. Furthermore, as discussed above, the samples migrating from capillaries 1a to 1t flow along the stream over capillaries 2a to 2t, passing though the gaps 3a to 3t under the sheath flow condition; then they are led into respective capillaries. Namely, samples migrating through the capillaries and gaps are made to migrate without contacting the samples migrating in the adjacent gaps. This permits fluorescence detection of the samples migrating in each gap, without being affected by the samples migrating in the neighboring gaps. In addition, the samples do not contact the inner surface of optical cell 104a; this feature eliminates the influence of the samples being absorbed to the optical cell 104a, and provides spatial removal of the scattered light on the surface of the optical cell 104a by means of slits or similar device. Thus, highly sensitive fluorescence detection is possible.

Introduction of the DNA fragments labeled by fluorophores is made possible by immersing one end of the capillary 1a on the cathode side into the sample solution, and by application of the 6 kV-voltage between the sample solution and the vessel for anode electrode 107 for about 20 seconds. After that, the end of the capillary is put back to the original position of the vessel for cathode electrode 106. This procedure is repeated for each of capillaries 1a to 1t, to supply samples into the capillary gels of capillaries 1a to 1t. Note that samples may be supplied to each capillary in sequence, as described above, or they may be supplied by immersing each of capillaries 1a to 1t into the sample solution and by simultaneous application of voltage. The samples poured in each of the capillaries 1a to 1t are made to move from the cathode to anode by application of the 6 kV-voltage between the vessel for cathode electrode 106 and the vessel for anode electrode 107 inside the capillary gels of the capillaries 1a to 1t, and pass through gaps 3a to 3t. Samples passing through gaps 3a to 3t are detected by irradiating He—Ne laser light having a wavelength of 594 nm to excite the Texas Red (Sulforhodamine 101) which is a labeling fluorophore. The laser light is adjusted so that the laser light irradiates gaps 3a to 3t arranged in a straight line simultaneously or under much the same conditions (laser light diameter), and the laser light is irradiated, thereby permitting fluorescence to be detected. Namely, laser light 21 having a wavelength of 594 nm of the He—Ne laser source 20 is condensed by lens 22 and irradiated to excite the DNA fragments labeled by fluorophores passing through gaps 3a to 3t. The laser having a beam diameter of about 0.7 mm, and the lens 22 having a focal distance of 100 mm are used, and the focus is set to the mid-position between gaps 3a and 3t. In this case, spot size of the laser light at the focal point is about 150 µm, and focal depth is about 20 mm. The distance between gap 3a and 3t is equal to the distance from capillary 1a to capillary 1t. In the case of the present embodiment, it is 0.6 mm by 19, namely about 12 mm. That is, the laser light irradiates 20 positions of the gaps 3a to 3t with much the same spot size, which is much the same as that of the capillary gel (100 µm). As discussed above, the spot size of the laser light can be much the same as that of the capillary gel. Uniform and efficient excitation of the DNA fragments labeled by fluorophores which migrate through gaps 3a to 3t by selecting the light source and lens system so that all gaps are irradiated with much the same spot size.

The fluorescence emitted from the DNA fragments labeled by fluorophores which migrate through gaps 3a to 3t is detected from the position perpendicular to the direction of laser irradiation. This configuration is illustrated in FIG. 4. After the background such as scattered light has been eliminated through interference filter 32, fluorescence 30 emitted from the DNA fragments, and forms the image on two-dimensional detector 34 such as CCD camera through lens 33. Being controlled by controller 35, two-dimensional detector 34 detects the fluorescent image of gaps 3a to 3t, and provides continuous and simultaneous detection of the change of the fluorescence intensity according to all gaps 3a to 3t, using data processor 36 of the computer or the like. These results are displayed on monitor 37, and are output on printer 38 or stored in memory 39. This feature permits simultaneous and continuous detection of migration patterns for each of capillaries 1a to 1t. Note that, in the case of the present embodiment, the one-dimensional detector such as a photodiode array can be used, instead of the two-dimensional detector such as a CCD camera, since the fluorescent images of the gaps are arranged on the one-dimension basis. For effective detection of the fluorescence emitted from the Texas Red, interference filter 32 uses the band pass interference filter which permits transmission of a wavelength band ranging from 610 to 630 nm.

The magnification of the lens is set so that the image of gaps 3a to 3t will be condensed on the photo-detecting surface of the two-dimensional detector. In the configuration shown in FIG. 4, fluorescence from the linear laser irradiation region may be collected by the cylindrical lens, as in the case of Embodiment 1, for which the fluorescence detection system shown in FIG. 1. Since (he reaps are filled with buffer solution in the present embodiment, the laser light irradiates gaps, without being affected by scattered light of the capillaries. This permits simultaneous, homogenous and efficient irradiation of samples migrating through two or more capillaries. It leads to substantial reduction of such background as scattered light and fluorescence from capillaries and capillary gels, ensuring highly sensitive fluorescence detection. The effect of reducing the background light is described: Compared with the case where fluorescence detection is made by shedding the laser light on the capillary itself the coating of which is removed, for example, fluorescent detection made at the gap as in the present embodiment reduces the detected background intensity to about one tenth or less, permitting detection of samples with smaller concentration. Arrangement of two or more gaps in a straight line enables simultaneous and simple irradiation of all gaps by the laser light, allowing simple apparatus configuration. Since two or more pairs of capillaries can be held in one optical cell, only one tube is sufficient for supply of sheath solution. Sheath flow occurs only at the position close to the gaps, flow rates are the same for all gaps, resulting in greater reproducibility. The optical cell according to the present embodiment has a simple structure; it is not necessary to use the optical cell of complicated configuration as found in the sheath flow chamber. In the present embodiment, the sample migration position can be determined by holding a pair of capillaries face to face with each other at a specified gap, and two or more capillaries (the space between the adjacent capillaries set at 0.6 mm in the present embodiment) can be laid out at positions close to each other. This allows reduction in the size of the optical cell. This also makes it possible to reduce the laser light further to irradiate two or more gaps. Excitation light density is increased, and fluorescence measurement is facilitated.

According to the present embodiment, buffer solution can be made to flow without using the mechanical means such as a liquid chromatography pump. This simplifies the apparatus configuration, and reduces the production cost. There is no pulsating flow which may occur when the pump is used; this ensures a stable flow of sheath solution and reduced feed rate variation, and reduced variations of fluorescence intensity of samples flowing in the gaps, resulting in detection accuracy. The flow rate of sheath solution can be easily adjusted by changing the head between the sheath solution level in the sheath solution bottle and buffer solution level in the vessel for an anode electrode on the downstream side for migration. This adjustment is also possible by changing the inner diameter of the capillary on the downstream side for migration. It is possible to make the sheath solution flow by using a mechanical means such as a liquid chromatography pump. In this case, the advantage is that the flow rate can be set directly. However, fluorescent intensity tends to change due to pulsating flow of the pump, so such treatment as smoothing in data processing is essential.

The sheath solution in the optical cell passes through capillaries 2a to 2t on the downstream side and flows out of the cell. Since the capillary generally has a small inner diameter, the flow rate at the capillary is generally small. Therefore, the volume of the sheath solution can be reduced, resulting in improved maneuverability. In the present embodiment, processing is made to ensure that the interior of capillaries 2a to 2t is positively charged, that the electroosmotic flow inside the capillaries 2a to 2t is directed toward the vessel for anode electrode, and that there is no reverse flow from capillaries 2a to 2t to the gaps. This ensures a stable flow of the sheath solution to vessel for anode electrode even when the flow rate of the sheath solution is small. If the inner diameter of capillaries 2a to 2t is great and the flow rate of the sheath solution in the gap is increased, the effect of the electroosmotic flow is reduced; as a result, treatment of the inner sides of capillaries 2a to 2t is not necessary.

In the present embodiment, sheath solution and buffer solution in the vessel for a cathode electrode and the vessel for an anode electrode use the same components as that of the buffer solution of the capillary gel. This prevents the capillary gel components from leaking into optical cell 104a or the electrode vessel, and permits reuse of the capillary gel, resulting in stable electrophoresis featuring high separative power. It is also possible to use the buffer solution which does not contain urea, namely, DNA denaturant, but urea inside the capillary gel may flow out from the capillary gel into the electrode vessel and fluorescent cell with the lapse of time. In this case, electrophoresis is possible as in the case of the buffer solution containing urea; however, the frequency of repeated use will reduce to some extent.

The used laser light source and fluorophores are not restricted to He—Ne laser and Texas Red (Sulforhodamine 101); any fluorophores and any suitable laser light source can be used. The present embodiment has been described based on the detection of the DNA fragments, but the principle applies to the analysis of the protein and similar substances. In the present embodiment, two capillaries having the same inner diameters have been used; a combination of different inner diameters is also possible. For example, if the inner diameter of the capillary on the downstream side is made smaller than that on the upstream side, the concentration of the sample solution will be increased when samples migrating from the end of the upstream capillary are lead into the downstream capillary, resulting in increased sample concentration, hence highly sensitive detection.

If the inner diameter of the capillary on the downstream side is made larger than that on the upstream side, samples migrating from the upstream capillary can be lead into the downstream capillary with greater ease and reliability.

Moreover, since fluorescence from the sample can be detected without the excitation light passing through the capillary region according the present embodiment, the capillary need not be transparent. The capillary coating need not be removed; this ensures handling ease. Furthermore, it also allows use of the capillary made of opaque fluorine-contained polymer such as tetrafluoroethylene polymer tube and tri-fluoro ethylene chloride polymer.

The capillary made of fluorine-contained polymer features little suction of samples, eliminating the need of treatment such as surface treatment. It is also very resistant against damage and chemicals, so use of fluorine-contained polymer capillaries provides excellent maneuverability, and permits use of solvents over an extensive range of pH values. In the present embodiment, the case of two or more pairs of capillaries has been explained. In the case of one pair of capillaries, eleclrophoresis separation of samples, detection of the fluorescence and detection of sample separation pattern are possible in the same way. In this case, the photomultiplier can be used as the optical detector.

[EMBODIMENT 3]

The following describes the DNA sequence determination method using the apparatus introduced in Embodiment 2. DNA fragments labeled by fluorophores are prepared by DNA polymerase reaction, using the primer labeled by fluorophore according to the well-known dideoxy sequencing method invented by Sanger and his colleagues. The primer bonded with Texas Red (Sulforhodamine 101, maximum emission wavelength of 615 nm) is used as primer. Firstly, the labeled primer is added to the single-strand DNA and annealed, so that labeled primer is bonded to the single-strand DNA. This reaction solution is divided into four parts, which are subjected to DNA polymerase reactions corresponding to A, C, G and T, respectively. That is, four types of deoxynucleotide triphosphates (dATP, dTTP, dCTP and dGTP) and ddATP which will be a terminator are added to the single-strand DNA bonded with labeled primer to cause DNA polymerase reaction. The above procedure provides DNA fragments labeled by fluorophores having various lengths with terminal A. Similar reactions are made for C, G and T. Four types of reaction solution obtained in the above procedure are poured into four of the capillaries 1a to it, for example, capillaries 1a, 1b, 1c and 1d, respectively. The pouring procedure is the same as given in Embodiment 2. Reaction solution A is put into capillary 1a, reaction solution C into 1b, reaction solution G into 1c and reaction solution T into 1d. After that, about 6 kV-voltage is applied to cause electrophoresis. Using the He—Ne laser having a wavelength of 594 nm to excite Texas Red (Sulforhodamine 101), change of the intensity of fluorescence in gaps 3a to 3d is measured with respect to time. Since the DNA fragments having smaller molecular weight are made to migrate earlier, the base sequence is determined by analyzing the fluorescence intensity at each gap according to time sequence. The apparatus shown in Embodiment 2 has 20 capillaries in which samples can be poured. Said DNA base sequence determination method allows simultaneous determination of base sequence of five types of DNA samples. This permits determination of the base sequence of more DNA samples by increasing the number of pairs of capillaries held in the optical cell.

In the present embodiment, the Texas Red (Sulforhodamine 101) is used as fluorophore. However, it is also possible to detect fluorescence emitted from two or more fluorophores. In that case, for example, it is possible to take either of the following steps:

(1) the optical detector sets comprising interference filter 32, lens 33 and detector 34 are prepared in numbers corresponding to that of the fluorophores, and each of the said detector sets is made to detect fluorescences of separate wavelength bands as shown in FIG. 4, or (2) the splitting prism is installed after lens 33 to separate light into spectral components, and the image of each component is formed on the two-dimensional detector such as a camera. Then fluorescence intensity is measured for each migration lane and wavelength.

Thus, the DNA base sequence can be determined even when the apparatus which provides simultaneous detection of two or more fluorophores has been configured. That is, each DNA is subjected to polymerase reaction, using primers labeled by different fluorophores for each type of the terminal base. Then reaction solutions are mixed and electrophoresis is carried out; then fluorescence of the DNA fragments passing through the gap spaces is detected. The base type can be identified by identifying the fluorophore types, whereby the base sequence is determined.

The fluorophore types can be identified by comparing the fluorescences at the maximum emission wavelength of four types of fluorophores. In this case, the base sequence of the DNA samples can be determined in the migration lane comprising a pair of capillaries and gaps. When two or more migration lanes are present as shown in FIG. 3, the base sequence of two or more DNA samples can be determined simultaneously in the number corresponding to the number of the migration lanes.

[EMBODIMENT 4]

Figure 5:
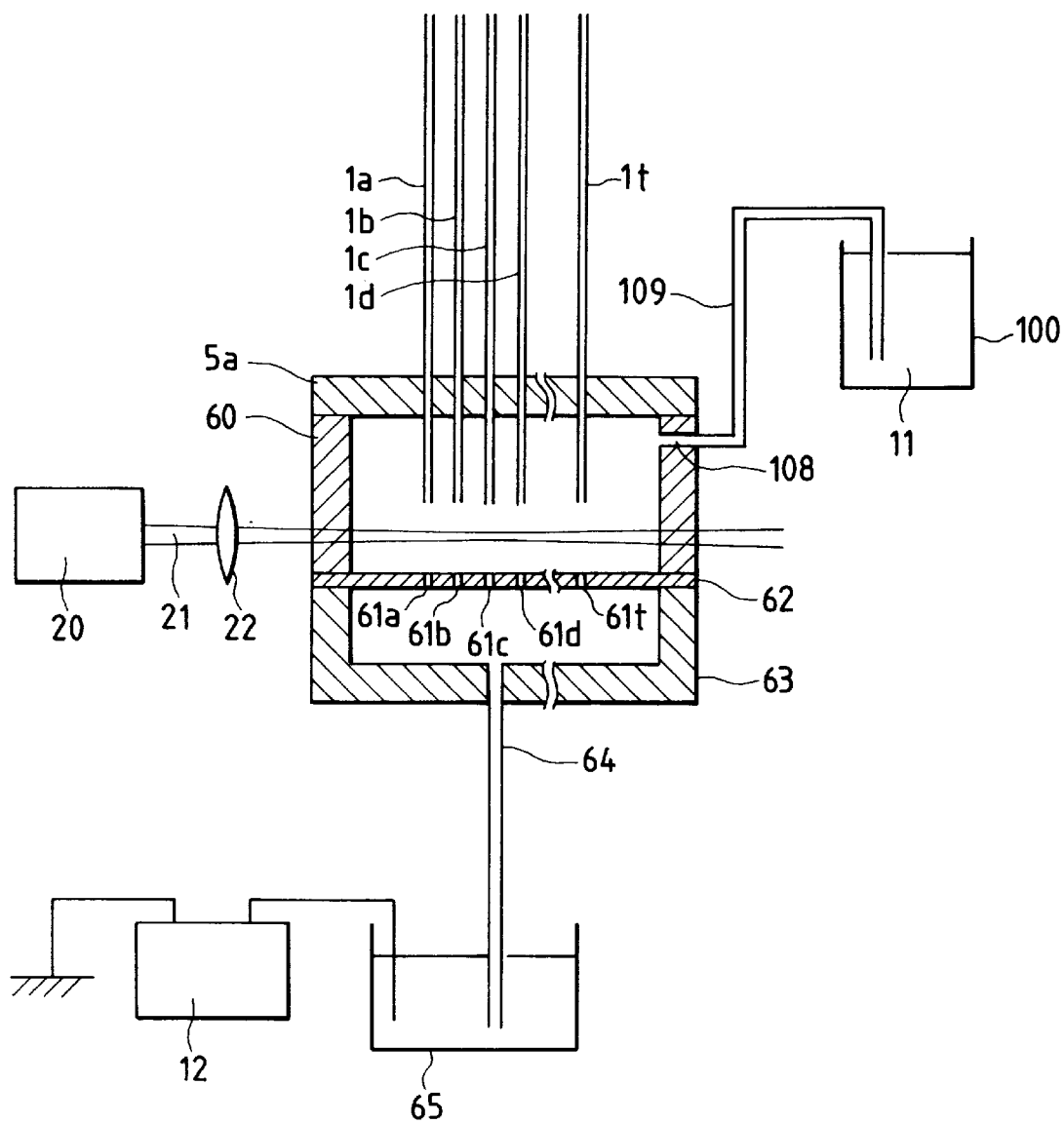
FIG. 5 is a block diagram representing the electrophoresis region and laser irradiation system of the electrophoresis apparatus according to the fourth Embodiment of the present invention.

The gap is formed by a pair of capillaries in said Embodiments 2 and 3, but the gap can also be made by other than the capillary pair. For example, the molecular weight separation region is composed of capillaries, as in said Embodiments. A gap can be formed by the end of these capillaries and the plate provided with fine holes. FIG. 5 shows the configuration of the elelrophoresis region and laser irradiation system of the eleclrophoresis apparatus according to the fourth Embodiment. As in the case of Embodiment 2, twenty capillaries 1*a* to 1*t* as electrophoresis separation region are held by the multi-capillary holder 5*a* and are fixed to the optical cell 60. The plate 62 provided with fine holes 61*a* to 61*t* having an inner diameter of 200 $\mu$m is fixed on the side opposite to the optical cell 60. Fine holes 61*a* to 61*t* are provided at the positions respectively corresponding to capillaries 1*a* to 1*t*, resulting in formation of the gaps. When the sheath solution flows, the sample migrating from each capillary is led to each corresponding fine hole. The vessel for trapping solution 63 is laid out below plate 62 to temporarily store the solution coming from the fine holes, and the solution is then led to the vessel for electrode 65 through tube 64.

Electrophoresis is performed in the same way as in Embodiment 2, by applying power to the vessel for electrode 65 and another vessel for electrode (not illustrated). Irradiation of laser and detection by fluorescence are also performed as in the case of the Embodiment 2.

[EMBODIMENT 5]

Figure 6:
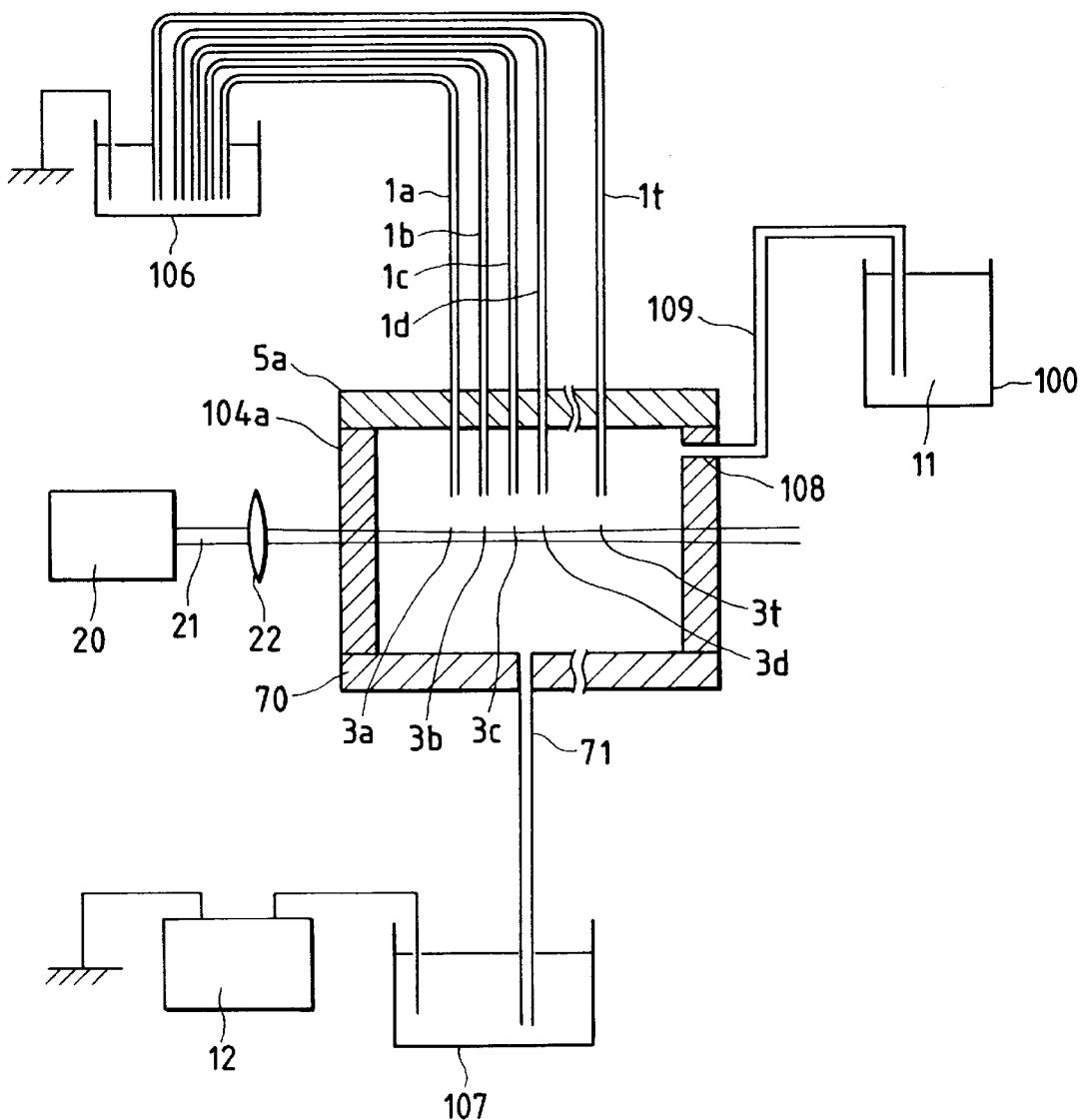
FIG. 6 is a block diagram representing the electrophoresis region and laser irradiation system of the electrophoresis apparatus according to the fifth Embodiment of the present invention.

In Embodiment 2, it is also possible to design a configuration where the samples are migrated by the flow of sheath solution, using only the upstream capillaries, without using the downstream ones. FIG. 6 shows the configuration of the eleclrophoresis region of the electrophoresis apparatus. As in the case of Embodiment 2, ends of capillaries 1*a* to 1*t* are arranged and held in the optical cell 104*a*.

The bottom of optical cell 104*a* is connected with the seal plate 70 and tetrafluoroethylene polymer tube 71, and the end of tetrafluoroethylene polymer tube 71 is immersed in the vessel for anode electrode 107, to permit flow of sheath solution. Sheath solution is poured in optical cell 104*a* in the same way as in the case of the Embodiment 2.

Electrophoresis is performed by DC voltage applied from DC high voltage power supply 12 between the vessel for cathode electrode 106 and the vessel for anode electrode 107. Immediately below the capillaries, samples which migrate from capillaries do not contact these samples which migrate through other capillaries; they migrate through the optical cell 104*a*, finally going to the vessel for anode electrode 107. Samples are detected by irradiating the laser light to 500 $\mu$m downstream of the ends of the capillaries in optical cell 104*a*, and by receiving fluorescence.

The photodetecting system is designed in the same configuration as in Embodiment 2. The sheath flow formation method of the present Embodiment is basically different from that of Embodiment 2. In the present Embodiment, sheath solution flows in the entire optical cell in a laminar flow. As a result, the flow rate of the sheath solution differs slightly, depending on the position inside the optical cell, and the sample migration lane also tends to vary; such unstable conditions occur. In terms of sensitivity and simplicity in the apparatus configuration, however, almost the same results can be obtained as 1hose in Embodiment 2.

[EMBODIMENT 6]

Figure 7:
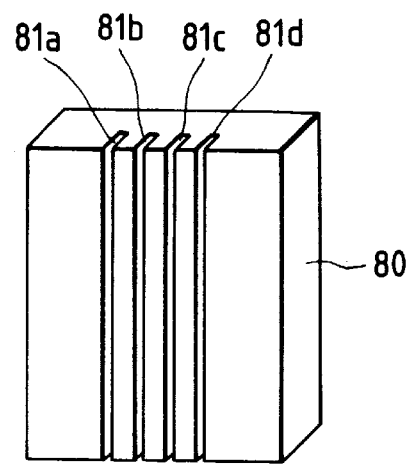
FIG. 7 is an oblique view representing the plate provided with two or more grooves according to the sixth Embodiment of the present invention.
Figure 8:
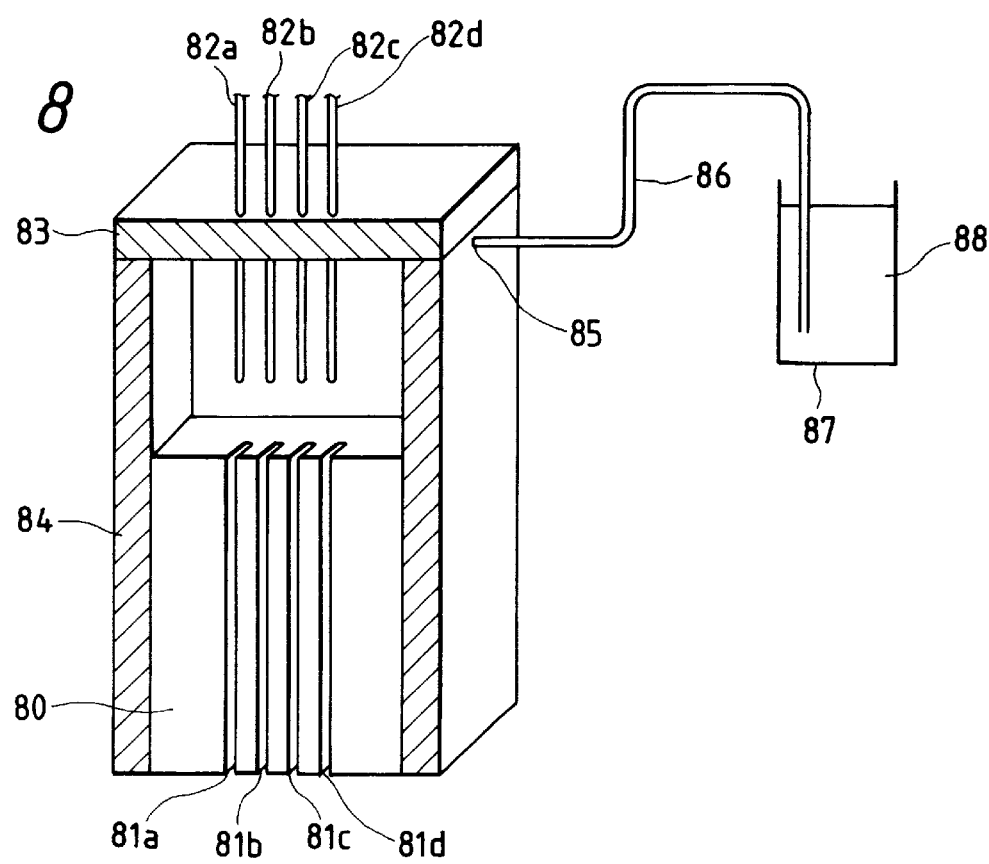
FIG. 8 shows the ootical cell of the electrophoresis region of the electrophoresis apparatus according to the sixth Embodiment of the present invention.

In the apparatus described in Embodiment 2, it is also possible to form the gap by using the plate provided with two or more grooves instead of the downstream capillaries. FIG. 7 is an oblique view of the plate provided with two or more grooves. Said Figure represents the case where four grooves corresponding to four capillaries are provided. Grooves 81*a*, 81*b*, 81*c* and 81*d* are formed on one side of the plate 80 conforming to the form inside the optical cell. The form of the groove is made to correspond to the size of the capillary for electrophoresis separation; for example, the groove is designed to have a width of 300 $\mu$m and a depth of 600 $\mu$m. The pitch distance between grooves is 1 mm. Note that the pitch and groove form can be changed as required. FIG. 8 is an oblique view showing the sectional area of the optical cell of electrophoresis region of the electrophoresis apparatus using the said plate. Optical cell 84 has inner dimensions of 20 mm in width, 3 mm in depth and 40 mm in length. The flow cell is used, which has the quartz glass plate having a thickness of 2 mm, with the top and bottom ends opened. Said Figure also shows the optical cell without the glass region located in its front. Plate 80 is inserted into optical cell 84 in close contact, so that the four lanes comprising the grooves 81*a*, 81*b*, 81*c* and 81*d*, and the glass (not illustrated) in front of the optical cell are formed. Capillaries 82*a*, 82*b*, 82*c* and 82*d* having an inner diameter of 100 $\mu$m and an outer diameter of 200 $\mu$m (gel formed inside in the same procedure as in Embodiment 2) are fixed inside the fluorescent cell 84 by multi-capillary holder 83. The pitch distance between the capillaries are 1 mm so as to match the pitch distance between grooves, and adjustment is made to ensure that the capillary axis is located at the center of each groove. This adjustment is achieved by adjusting the position of the holes on multi-capillary holder 83. Ends of capillaries 82*a*, 82*b*, 82*c* and 82*d* are arranged inside the multi-capillary holder 83, and adjustment is made so that each capillary end will be about 1 mm away from plate 80; then capillaries are fixed in the optical cell.

Electrophoresis is made possible by bringing the bottom of the optical cell 84 in contact with the buffer solution inside the vessel for the anode electrode. As in the case of Embodiment 4 or 5, it is also possible to connect it to the vessel for the electrode through the tube. Sheath solution is poured in the same way as in the case of the Embodiment 2. Samples migrating from the capillaries 82*a* to 82*d* are held in the sheath solution and made to flow into optical cell 84; they are then led to the vessel for the anode electrode through grooves 81*a*, 81*b*, 81*c* and 81*d*.

Electrophoresis, laser irradiation and fluorescence detection are performed in the same method as in the case of the Embodiment 2; the method provides an effective and simultaneous detection of samples separated respectively by two or more capillaries. In the present Embodiment, the downstream side is formed by the plate constituting the grooves, not by the capillaries. This allows easy adjustment of the distance between each capillary end and the plate end ends of the grooves. The plate is preferred to be made of quartz glass, where fluorescence is not caused by laser irradiation.

[EMBODIMENT 7]

Figure 9:
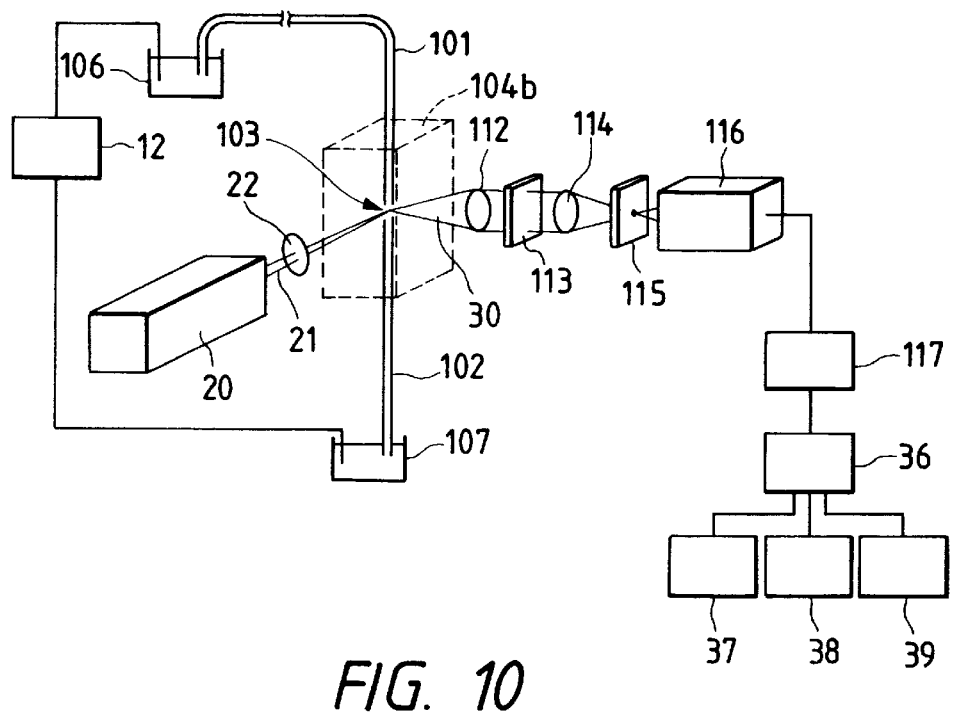
FIG. 9 is a block diagram representing the electrophoresis apparatus according to the seventh Embodiment of the present invention.

In the present Embodiment, the DNA fragments labeled by fluorophores are separated by electrophoresis and are detected by fluorescence. Fluorescence detection is made at the region where the samples separated by electrophoresis in the capillary migrate from the capillary end into the buffer solution. The following describes the case of using the Texas Red (sulforhodamine 101) for labeling fluorophores:

FIG. 9 illustrates the configuration of the electrophoresis apparatus of the present Embodiment. It uses two capillaries; a silica capillary 101 having an inner diameter of 100 μm, outer diameter of 375 μm and length of 30 cm and a silica capillary 102 having the same inner and outer diameters with a length of 5 cm. Five percent polyacrylamide gel containing urea as denaturant is produced in capillaries 101 and 102, as in the case of the capillaries 1a and 1b in Embodiment 2.

Each one end of capillaries 101 and 102 is held face to face with the other in the optical cell, and the samples are detected using detection of fluorescence. That is, each one end of capillaries 101 and 102 is held face to face coaxially with the other forming a 0.1 nm gap 103 inside rectangular quartz optical cell 104b (outer 3 mm square, inner 1 mm square), and the gap space is used as an optical detecting portion. The other ends of capillary 101 and capillary 102 are immersed respectively in the vessel for cathode electrode 106 and the vessel for anode electrode 107 filled with buffer solution (TRIS-borate-EDTA buffer solution). Buffer solution containing glycerin is poured into optical cell 104b, and gap 103 is filled with buffer solution. DC high voltage is applied between the vessel for cathode electrode 106 and the vessel for anode electrode 107 by DC high voltage power supply 12. When the voltage is applied, current runs through capillary 102, gap 103 and capillary 101. Gap 103 is short and, in gap 103, current flows along the line connecting the axes of capillary 102 and capillary 101. So the migrating sample flows out of capillary 101, and passes through gap 103 without much dispersion, flowing into capillary 102. That is, the sample migrates without contacting the optical cell 104b.

Buffer solution containing glycerin has been poured into optical cell 104, namely, gap 103; addition of glycerin is intended to reduce the influence of convection due to increased viscosity of buffer solution and to improve the electric field intensity in gap 103. Controlled convection of the buffer solution and increased electric field intensity reduces the dispersion of the sample in gap 103, allowing easy migration of the sample from capillary 101 to capillary 102.

Glycerin is used in the present Embodiment. Other substances can be used if they have high viscosity and are usable for electrophoresis. For example, polyethylene glycol or succrose etc. can be used. If gap 103 is sufficiently narrow, normal buffer solution without glycerin may be used. To introduce DNA fragments labeled by fluorophores which are samples, one end of capillary 101 on the cathode side is immersed in the sample solution temporarily, and 5 kV voltage is applied between the sample solution and the vessel for anode electrode 107 for about 20 seconds. Then the end of capillary 101 is returned to the vessel for cathode electrode 106, and 10 kV DC voltage is applied between the vessel for cathode electrode 106 and the vessel for anode electrode 107. Then the samples migrate from cathode to anode sides in capillary 101 while undergoing molecular weight separation, and pass through gap 103.

Laser light 21 having a wavelength of 594 nm from the He—Ne laser source 20 is condensed to about 20 μm by lens 22, and is irradiated on the gap 103. Fluorescence 30 issued from the DNA fragments is collected by lens 112 from the direction perpendicular to the direction in which laser light is irradiated. Backgrounds such as scattered light are eliminated by interference filter 113, and the image is formed on slit 115 by lens 114. The light passing through slit 115 is detected by photomultiplier 116, and amplified by amplifier 117; then the electrophoresis pattern is processed by data processor 118 of the computer or the like, and their results-are displayed on monitor 37, and are output on printer 38 or stored in memory 39.

To ensure effective detection of the fluorescence issued from the Texas Read, interference filter 113 uses the band pass interference filter which permits transmission of a wavelength band ranging from 610 to 630 nm. Lens systems 112 and 114 are configured to have the equal magnifications.

The opening of slit 115 is set to 50 μm in the direction of electrophoresis and 100 μm in the direction of laser light, and adjustment is made to ensure that fluorescent image in gap 3 is located at the center of the opening. Since samples migrate only close to gap 3, the image of the scattered light of the laser light at optical cell 104b is not formed on the opening of slit 115 and is not detected by the photomultiplier 116 because of the configuration of said optical system. Scattered light and fluorescence are not produced by the capillary and gel, resulting in substantially reduced background intensity.

Figure 10:
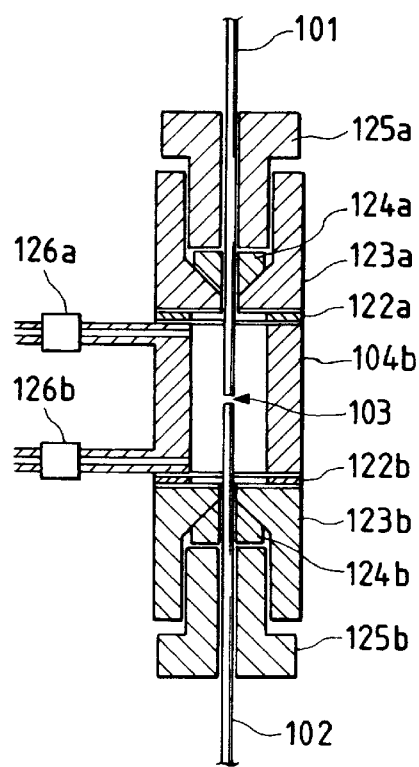
FIG. 10 is an enlarged view representing the optical cell according to the seventh Embodiment of the present invention.

FIG. 10 is an enlarged view representing the sectional area of the optical cell 104b. Quartz optical cell 104b is fixed by multi-capillary holders 123a and 123b. Liquid leakage is prevented by insertion of the silicone rubber packings 122a and 122b between optical cell 104b and holders 123a and 123b. Capillary 101 is fixed to multi-capillary holders 123a by tetrafluoroethylene polymer ferrule 124a and screw 125a. Likewise, capillary 102 is also fixed by ferrule 124b and screw 125b. The gap between capillary 101 and capillary 102 can be freely adjusted by specifying the length of the capillary from the ferrule. In the present Embodiment, this is 0.1 mm, as described previously. The optical cell is provided with solution inlet to pour buffer solution. It is also connected with the valves 126a and 126b. The buffer outlet can be provided at the optical cell holder. Optical cell 104b is filled with buffer solution after fixing the capillary.

DNA fragments labeled by fluorophores can be detected by the apparatus in the present Embodiment. The DNA fragments labeled by fluorophores area prepared according to the well-known dideoxy sequencing method invented by Sanger and his colleagues, under the same conditions as in the case of the Embodiment.

As discussed above, the DNA fragment electrophoresis pattern can be measured by introducing the samples into the capillary and measuring the fluorescence intensity in the gap. As in the case of the Embodiment 2, compared to the case of fluorescence detection by irradiating the laser light on the capillary without coating, the background intensity is reduced by about one tenth or less in the present Embodiment, permitting detection of samples of less concentration.

The method according to the present Embodiment provides highly sensitive detection of samples using the gel, without loss of electrophoresis characteristics. The buffer solution is not made to flow, so a simple apparatus configuration can be obtained. The laser equipment and fluorophores to be used are not restricted to He—Ne laser and Texas Red (sulforhodamine 101); any fluorophores and any suitable laser light source can be used. Furthermore, as in the case of the Embodiment 3, the present method provides simultaneous fluorescence detection of two or more fluorophores.

When the DNA base sequence is to be determined using the two or more fluorophores in the apparatus according to the present Embodiment, exactly the same procedure as in the case of the Embodiment 3 is used. The present Embodiment has been explained with reference to the detection of DNA fragments, but the same method is applicable also to the analysis of protein, sugar and similar substances. Furthermore, two capillaries having the same inner diameter have been used for the description of the present Embodiment. It is also possible to use a combination of capillaries having different inner diameters. The effect resulting from the difference between the inner diameters of capillaries 101 and 102 is the same as that described with reference to Embodiment 2. Furthermore, the method for the present Embodiment permits detection of the fluorescence without the excitation light passing through the capillary region, so the capillary need not be transparent; the capillary coating need not be removed. It allows use of capillaries made of an opaque fluorine-contained polymer such as tetrafluoroethylene polymer or trifluoro ethylene chloride polymer.

[EMBODIMENT 8]

Figure 11:
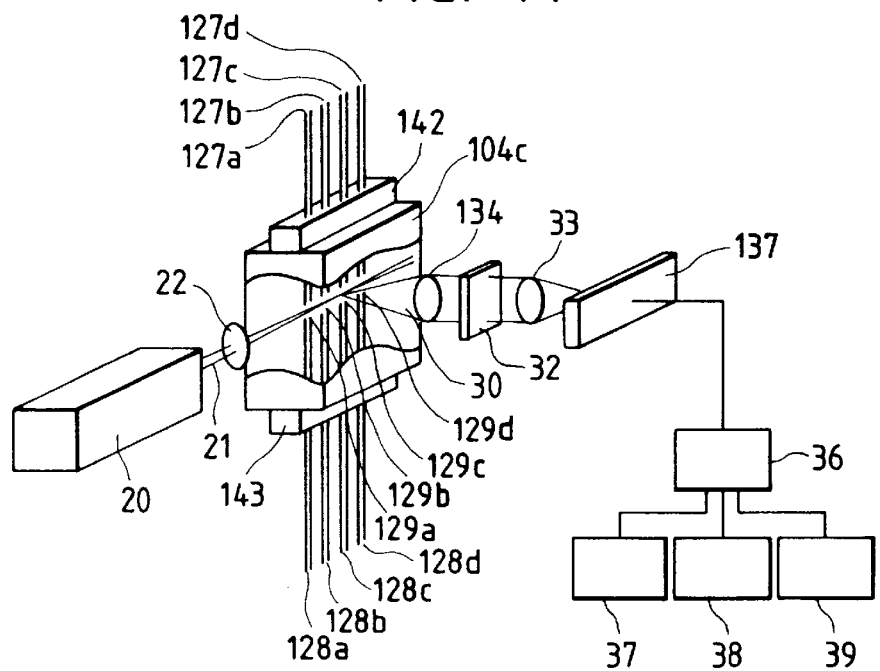
FIG. 11 is a block diagram representing the electrophoresis apparatus according to the eighth Embodiment of the present invention.

The following describes the simultaneous fluorescence detection apparatus with four capillaries arranged in parallel. The number of capillaries is not limited to four; it can be any number. FIG. 11 shows the configuration of the electrophoresis apparatus for the present Embodiment. The 127a, 127b, 127c and 127d in the Figure denote silica capillaries having an inner diameter of 100 μm, outer diameter of 375 μm and length of 30 cm. One end of each of the capillaries (not shown) is immersed in the vessel for the cathode electrode as in the case shown in FIG. 9. Likewise, 128a, 128b, 128c and 128d denote the silica capillaries having the same inner and outer diameters with a length of 5 cm, and one end of each is immersed in the vessel for the anode electrode (not shown). According to the same method as given in the Embodiment 2, five percent polyacrylamide gel containing urea as denaturant is produced in these capillaries.

Each capillary is provided with silane coupling treatment so that polyacrylamide gel and capillary wall are chemically bonded together, with consideration given so as not to allow the capillary to elude from the acrylamide during electrophoresis.

Capillary 127a to 127d and capillaries 128a to 128d are held and fixed in rectangular quartz optical cell 104c, maintaining gaps 129a to 129d of specified intervals, as in the case of the Embodiment 7, and are arranged in a straight line in close proximity with each other, forming two or more gaps, namely, optical detecting portions.

The capillaries are fixed by the capillary holders 142 and 143 of the block made of fluorine-contained polymer such as tetrafluoroethylene, provided with four vertical holes at intervals of 1 mm. Each capillary is inserted into each of four vertical holes, and adjustment is so made that 127a and 128a, 127b and 128b, 127c and 128c, and 127d and 128d are respectively coaxial, and that each length of gaps 129a to 129d will be 0.2 mm.

Buffer solution containing glycerin is poured into the optical cell 104c, filling gaps 129a to 129d with buffer solution. If voltage is applied under this condition, the sample led into capillary 127a migrates to gap 129a, then to 128a. Samples led to other capillaries also migrate in the same way. The glycerin in the buffer solution restrains the convection of the buffer solution in gaps, as in the case of embodiment 7 and ensures reliable and smooth migration of the sample from capillaries 127a to 127d to capillaries 128a to 128d.

Fluorescent detection of the DNA fragments passing through gaps 129a to 129d is carried out as follows: Firstly, laser light 21 from laser source 20 is condensed by lens 22 to permit simultaneous irradiation of two or more optical detecting portions, namely, gaps 129a to 129d. The focal point is set at the mid-position between the gaps 129b and 129c, and adjustment is made to ensure that the maximum diameter of the irradiated spot size is 100 μm between gaps 129a to 129d. When the focal distance of about 150 mm is used as lens 22, for example, it is possible to irradiate gaps 129a to 129d with much the same spot size.

Fluorescence 30 emitted from DNA fragments passing through each gap is collected by lens 134 from the position perpendicular to the direction in which the laser is irradiated, and the background such as scattered light is removed by the interference filter 32. Then it is collected by lens 33, and the image is formed on line sensor 37 such as a photodiode array or CCD camera. In the configuration in FIG. 11, using the fluorescence detection system as in the case of the Embodiment 1 shown in FIG. 1, it is also possible to collect the fluorescence from the linear laser irradiation region by the cylindrical lens. After the data is output from the output of line sensor 37, the electrophoresis pattern and the like is subjected to data processing by data processor 36 of the computer or similar device, and their results are displayed on monitor 37, and are output on printer 38 or stored in memory 39.

Using the He—Ne laser having a wavelength of 594 nm as a laser light and Texas Red (sulforhodamine 101) solution as sample, the sample is made to migrate in capillaries 127a to 127d. When fluorescent images of samples migrating in gap spaces which are optical detectors are detected by the line sensor 37, strong fluorescence intensity is detected in four positions of the gaps 129a to 129d, namely, optical detecting portions corresponding to migration lanes, each independently of the other optical detecting portions. Continuous and simultaneous detection of the samples migrating in the capillaries is possible by detecting the intensity of the signals at the positions corresponding to migration lanes on the line sensor.

The method according to the present Embodiment allows fluorescence detection of samples migrating simultaneously and under the same conditions by two or more optical detectors. It also allows analysis over an extensive range, for example, DNA base sequence determination for one or more samples, analysis of the side strand or functional group using the fluorophores, and detailed analysis of the samples separated by liquid chromatography. Furthermore, pairs of capillaries are arranged in a straight line in close proximity to form two or more gaps, so only one fluorescence collecting means such as a lens is sufficient; this feature ensures reduced cost and simple structure.

Furthermore, as in the case of the preceding Embodiments, laser light is irradiated along the gaps where there is no capillary. Then the laser is not scattered or refracted by the capillary, so each gap can be irradiated by much the same spot size, with much the same intensity and reduced background intensity. This permits simple configuration of the apparatus which provides effective excitation of two or more samples, hence highly sensitive detection. Such an apparatus facilitates simultaneous detection of many samples.

The DNA base sequence determination method using the apparatus according to the method of the present Embodiment is the same as that of Embodiment 3. Use of the Texas Red (sulforhodamine 101, maximum emission wavelength: 615 nm) as a labeling fluorophore, and the He—Ne laser having a wavelength of 594 nm as an excitation light source is especially preferred to ensure high sensitivity.

[EMBODIMENT 9]

Figure 12:
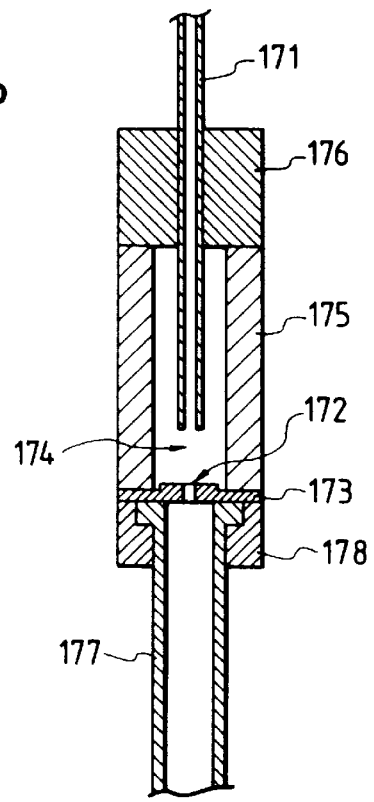
FIG. 12 is an enlarged view representing the optical cell according to the ninth Embodiment of the present invention.

The gap is formed by a pair of capillaries in said Embodiments 7 to 8, but it can also be by other substances than capillaries. For example, the electrophoresis separation region is composed of capillaries, as in said Embodiments. A gap can be formed by the end of these capillaries and the plate provided with fine holes. FIG. 12 is an enlarged view representing the sectional area of the optical cell in which the gap is formed by a capillary and the plate provided with fine holes.

As in the case of the Embodiment 7, capillary 171 filled with polyacrylamide gel and plate 173 provided with fine holes 172 (for example, a plate made of tetrafluoroethylene polymer) are arranged face to face so that the axis of capillary 171 and that of fine hole 172 will be almost matched to each other, and gap 174 is formed. They are held inside the optical cell 175. This cell is a rectangular optical cell having outer dimensions of 3 mm square and inner dimensions of 1 mm square, with the top and bottom ends opened. It is held, for example, by tetrafluoroethylene polymer block 176 on the top, and held by plate 173 on the bottom and fixed, so that buffer solution can be stored in the cell. The tetrafluoroethylene polymer block 176 is provided with the hole conforming to the outer dimensions of capillary 171. Capillary 171 is passed through that hole to hold the capillary 171, and the length of gap 174 can be adjusted from 0.1 mm to 1.0 mm. The other end of capillary 171 is immersed in the vessel for the cathode electrode, as in the case of the Embodiment 7. The tetrafluoroethylene polymer tube 177 is connected to the bottom of plate 173 through tube holder 178, and is led to the vessel for the anode electrode. Plate 173 can also be made to contact with the vessel for the anode electrode. Although not shown in FIG. 12, the buffer solution inlet is provided inside fluorescent cell 175, as in the case of FIG. 10. The buffer solution is supplied through the valve during electrophoresis, to fill optical cell 175, gap 174 and tetrafluoroethylene polymer tube 177. After the supply of buffer solution is stopped, the sample is made to migrate. The method of the present Embodiment provides fluorescent detection with the minimum background intensity as in the case of Embodiment 7, and highly sensitive fluorescence detection.

Arrangement of fine holes on plate 173 in a straight line permits configuration of the optical cell which has the same effects as those in the case of the Embodiment 8.

The method of the present Embodiment ensures easy installation of the apparatus since plate 173 is used on one side.

As disclosed above, according to the present invention, one or more samples are separated by electrophoresis separation by using the plate gel or capillary gel, and the laser beam is irradiated linearly on the two or more migration lanes from the direction which is approximately perpendicular to the direction for sample migration and which is parallel to the surface formed by two or more migration lanes; thereby detecting fluorescence on a real-time basis from the fragments migrating two or more migration lanes. Use of Texas Red (sulforhodamine 101, maximum emission wavelength: 615 nm) as labeling fluorophore, and He—Ne laser light having an emission wavelength of 594 nm as an excitation light source is particularly preferred to ensure high sensitivity in Embodiments 1 to 9. In Embodiments 2 to 9, however, the fluorophore and light source to be used are not restricted to Texas Red and He—Ne laser having an emission length of 594 nm. For example, rhodamine derivatives, FITC, SF, TRITC and ALPC (aluminum phthalocyanine) complex (emission wavelength: about 700 nm) as fluorophore, and argon ion laser (emission wavelength: 488 nm and 514.5 nm), He—Ne laser (emission wavelength: 632.8 nm), YAG laser (second harmonic wavelength: 532 nm) and semiconductor laser (emission wavelength: about 670 nm) as the laser light source can be used.

What is claimed is:

1. A method for analyzing samples comprising the steps of:

introducing samples labeled with fluorophores into a first end of each of a plurality of electrophoresis lanes including a separation medium, a second end of each of the electrophoresis lanes being disposed in an optical cell filled with a buffer solution;

applying an electric field to the electrophoresis lanes to separate the samples labeled with the fluorophores and cause the separated samples labeled with the fluorophores to migrate through the electrophoresis lanes into the buffer solution in the optical cell;

exciting, with light from a light source, the fluorophores labeling the separated samples in the buffer solution in the optical cell to emit fluorescence in the buffer solution in the optical cell, the light source being selected from the group consisting of a He—Ne laser which emits light having a wavelength of 594 nm, a He—Ne laser which emits light having a wavelength of 632.8 nm, a YAG laser which emits light having a wavelength of 532 nm, and a semiconductor laser which emits light having a wavelength of 670 nm; and detecting, with a photodetector, the fluorescence emitted by the fluorophores labeling the separated samples in the buffer solution in the optical cell.

2. A method for analyzing samples comprising the steps of:

introducing samples labeled with fluorophores into a first end of each of a plurality of capillaries including a separation medium, a second end of each of the capillaries being disposed in an optical cell filled with a buffer solution;

applying an electric field to the capillaries to separate the samples labeled with the fluorophores and cause the separated samples labeled with the fluorophores to migrate through the capillaries into the buffer solution in the optical cell;

exciting, with light from a light source, the fluorophores labeling the separated samples in the buffer solution in the optical cell to emit fluorescence in the buffer solution in the optical cell, the light source being selected from the group consisting of a He—Ne laser which emits light having a wavelength of 594 nm, a He—Ne laser which emits light having a wavelength of 632.8 nm, a YAG laser which emits light having a wavelength of 532 nm, and a semiconductor laser which emits light having a wavelength of 670 nm; and detecting, with a photodetector, the fluorescence emitted by the fluorophores labeling the separated samples in the buffer solution in the optical cell.

3. A method for analyzing samples comprising the steps of:

introducing samples labeled with fluorophores into a first end of each of a plurality of electrophoresis lanes including a separation medium, a second end of each of the electrophoresis lanes being disposed in an optical cell filled with a buffer solution, there being a flow of the buffer solution in the optical cell;

applying an electric field to the electrophoresis lanes to separate the samples labeled with the fluorophores and cause the separated samples labeled with the fluorophores to migrate through the electrophoresis lanes into the flow of the buffer solution in the optical cell;

exciting, with light from a light source, the fluorophores labeling the separated samples in the flow of the buffer solution in the optical cell to emit fluorescence in the flow of the buffer solution in the optical cell, the light source being selected from the group consisting of a He—Ne laser which emits light having a wavelength of 594 nm, a He—Ne laser which emits light having a wavelength of 632.8 nm, a YAG laser which emits light having a wavelength of 532 nm, and a semiconductor laser which emits light having a wavelength of 670 nm; and detecting, with a photodetector, the fluorescence emitted by the fluorophores labeling the separated samples in the flow of the buffer solution in the optical cell.

4. A method for analyzing samples comprising the steps of:

introducing samples labeled with fluorophores into a first end of each of a plurality of capillaries including a separation medium, a second end of each of the capillaries being disposed in an optical cell filled with a buffer solution, there being a flow of the buffer solution in the optical cell;

applying an electric field to the capillaries to separate the samples labeled with the fluorophores and cause the separated samples labeled with the fluorophores to migrate through the capillaries into the flow of the buffer solution in the optical cell;

exciting, with light from a light source, the fluorophores labeling the separated samples in the flow of the buffer solution in the optical cell to emit fluorescence in the flow of the buffer solution in the optical cell, the light source being selected from the group consisting of a He—Ne laser which emits light having a wavelength of 594 nm, a He—Ne laser which emits light having a wavelength of 632.8 nm, a YAG laser which emits light having a wavelength of 532 nm, and a semiconductor laser which emits light having a wavelength of 670 nm; and detecting, with a photodetector, the fluorescence emitted by the fluorophores labeling the separated samples in the flow of the buffer solution in the optical cell.

* * * * *